(12) United States Patent
Drapeau et al.

(10) Patent No.: US 10,071,120 B2
(45) Date of Patent: Sep. 11, 2018

(54) BONE FIBER COMPOSITIONS

(71) Applicant: Warsaw Orthopedic, Inc., Warsaw, IN (US)

(72) Inventors: Susan J. Drapeau, Collierville, TN (US); Guobao Wei, Milltown, NJ (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 468 days.

(21) Appl. No.: 13/751,528

(22) Filed: Jan. 28, 2013

(65) Prior Publication Data
US 2014/0212471 A1 Jul. 31, 2014

(51) Int. Cl.
*A61K 35/32* (2015.01)
*A61L 27/36* (2006.01)

(52) U.S. Cl.
CPC .......... *A61K 35/32* (2013.01); *A61L 27/3608* (2013.01); *A61L 2430/02* (2013.01)

(58) Field of Classification Search
CPC ...... A61K 6/02; A61K 6/0205; A61K 6/0273; A61K 6/0643; A61K 9/141; A61K 9/143; A61K 9/146; A61K 9/16; A61K 9/1605; A61K 9/1625
USPC ................................................ 424/422–424
See application file for complete search history.

(56) References Cited

U.S. PATENT DOCUMENTS

| | | |
|---|---|---|
| 4,882,149 A | 11/1989 | Spector |
| 5,073,373 A | 12/1991 | O'Leary et al. |
| 5,417,975 A | 5/1995 | Lussi et al. |
| 5,573,771 A | 11/1996 | Geistlich et al. |
| 5,676,146 A | 10/1997 | Scarborough |
| 2002/0120348 A1* | 8/2002 | Melican ............... A61F 2/0045 623/23.72 |
| 2004/0078090 A1* | 4/2004 | Binette .................. A61L 27/36 623/23.76 |
| 2009/0130173 A1 | 5/2009 | Behnam et al. |
| 2009/0157087 A1 | 6/2009 | Wei et al. |
| 2009/0182427 A1* | 7/2009 | Liu ..................... A61B 17/7098 623/16.11 |
| 2009/0220605 A1* | 9/2009 | Wei ......................... A61F 2/28 424/486 |
| 2010/0203155 A1 | 8/2010 | Wei et al. |
| 2011/0054408 A1 | 3/2011 | Wei et al. |
| 2011/0070312 A1 | 3/2011 | Wei et al. |
| 2012/0009230 A1* | 1/2012 | Drapeau ................. A61L 27/20 424/400 |
| 2012/0041444 A1 | 2/2012 | Einhorn |
| 2012/0100225 A1* | 4/2012 | McKay ............. A61K 38/1875 424/549 |

OTHER PUBLICATIONS

Kidney Stones information sheet (Premier Urology Group, LLC; ww.urosurgery.info/kidney_stone.php).*
Kidney Stones (Premier Urology Group, LLC; ww.urosurgery.info/kidney_stone.php).*
Kidney Stones (Premier Urology Group, LLC; www.urosurgery.info/kidney_stone.php) (Year: 2010).*

* cited by examiner

*Primary Examiner* — Micah Paul Young

(57) ABSTRACT

An osteoinductive implantable composition comprising a mixture of demineralized bone fibers and mineralized bone fibers is provided. The mixture is visible under X ray and remodels more easily than comparable mixtures of demineralized bone matrix and surface demineralized cortical bone chips. The osteoinductive implantable compositions comprises demineralized bone fibers in an amount from about 30 vol % to about 45 vol % and mineralized bone fibers in an amount from about 55 vol % to about 70 vol %. The osteoinductive implantable compositions can be delivered in delivery systems including mesh coverings for administration at surgical sites. A method of treating a bone defect caused by injury, disease, wounds, or surgery utilizing the osteoinductive implantable composition comprising a mixture of demineralized bone fibers and mineralized bone fibers is also provided.

17 Claims, 5 Drawing Sheets

HUMAN FIBERS

MagniFuse-C: 10% demin fiber 90% mineralized fiber
3A

MagniFuse-C: 20% demin fiber 80% mineralized fiber
3B

MagniFuse-C: 30% demin fiber 70% mineralized fiber
3C

MagniFuse-C: 50wt% demin fiber 50% mineralized fiber
3D

MagniFuse Grafton from NC-11061A
3E

4B RABBIT CARTILAGE MILLED FIBER (MINERALIZED)

4A HUMAN CARTILAGE MILLED FIBER (MINERALIZED)

BONE FIBER COMPOSITIONS

FIELD

Bone fiber compositions and delivery systems for the same are provided. More particularly, bone fiber compositions include demineralized and mineralized bone fibers useful as implants in a variety of surgical procedures.

BACKGROUND

Mammalian bone tissue is known to contain one or more proteinaceous materials, presumably active during growth and natural bone healing that can induce a developmental cascade of cellular events resulting in endochondral bone formation. Various factors are present in bone. These include bone morphogenetic or morphogenic proteins (BMPs), bone inductive proteins, bone growth or growth factors, osteogenic proteins, or osteoinductive proteins. While these factors have different effects and functions, as discussed herein, these will be referred to collectively herein as osteoinductive factors.

It is known that bone contains osteoinductive factors. These osteoinductive factors are present within the compound structure of cortical bone and are present at very low concentrations, for example, 0.003%. Osteoinductive factors direct the differentiation of pluripotent mesenchymal cells into osteoprogenitor cells that form osteoblasts. Proper demineralization of cortical bone exposes the osteoinductive factors, rendering it osteoinductive.

The rapid and effective repair of bone defects caused by injury, disease, wounds, or surgery has long been a goal of orthopaedic surgery. Toward this end, a number of compositions and materials have been used or proposed for use in the repair of bone defects. The biological, physical, and mechanical properties of the compositions and materials are among the major factors influencing their suitability and performance in various orthopaedic applications.

Autologous cancellous bone ("ACB") long has been considered the gold standard for bone grafts. ACB includes osteogenic cells, which have the potential to assist in bone healing, is nonimmunogenic, and has structural and functional characteristics that should be appropriate for a healthy recipient. Some people do not have adequate amounts of ACB for harvesting. These people include, for example, older people and people who have had pervious surgeries. A majority of people however do have adequate amounts of ACB for harvesting. There may nevertheless be reluctance to harvest because of pain at the harvest site and potential donor site morbidity.

Conventionally, bone tissue regeneration is achieved by filling a bone repair site with a bone graft. Over time, the bone graft is incorporated by the host and new bone remodels the bone graft. In order to place the bone graft, it is common to use a monolithic bone graft or to form an osteoimplant comprising particulated bone in a carrier. The carrier is thus chosen to be biocompatible, to be resorbable, and to have release characteristics such that the bone graft is accessible.

The rapid and effective repair of bone defects caused by injury, disease, wounds, or surgery is a goal of orthopedic surgery. Toward this end, a number of compositions and materials have been used or proposed for use in the repair of bone defects. The biological, physical, and mechanical properties of the compositions and materials are among the major factors influencing their suitability and performance in various orthopedic applications.

Bone-related disorders are characterized by bone loss resulting from an imbalance between bone resorption and bone formation. Throughout life, there is a constant remodeling of skeletal bone. In this remodeling process, there is a delicate balance between bone resorption by osteoclasts and subsequent restoration by osteoblasts. Osteoblasts, involved in both endochondral and intramembraneous ossification, are the specialized cells in bone tissue that make matrix proteins resulting in the formation of new bone. Bone formation, i.e. osteogenesis, is essential for the maintenance of bone mass in the skeleton. Unlike osteoblasts, osteoclasts are associated with bone resorption and removal. In normal bone, the balance between osteoblast-mediated bone formation and osteoclast-mediated bone resorption is maintained through complex regulated interactions.

Bone grafting is used to repair bone voids that are extremely complex, pose a significant health risk to the patient, or fail to heal properly. This is done with materials either from the patient's own body or by using an artificial, synthetic, or natural substitute. Demineralized bone matrix (DBM) based materials are commonly used in these procedures to substitute for, or extend the volume of, autograft and local bone. Thus, demineralized bone matrix ("DBM") implants have been reported to be particularly useful. Demineralized bone matrix is typically derived from cadavers. The bone is removed aseptically and/or treated to kill any infectious agents. The bone is then particulated by milling or grinding and then the mineral components are extracted for example, by soaking the bone in an acidic solution.

Some DBM formulations have various drawbacks. For example, while the collagen-based matrix of DBM is relatively stable, the active factors within the DBM matrix are rapidly degraded. The osteogenic activity of the DBM may be significantly degraded within 24 hours after implantation, and in some instances the osteogenic activity may be inactivated within 6 hours. Therefore, the factors associated with the DBM are only available to recruit cells to the site of injury for a short time after transplantation. For much of the healing process, which may take weeks to months, the implanted material may provide little or no assistance in recruiting cells.

It has also been found that when bone implants contain a mixture of fibers and surface demineralized cortical bone chips, such implants remodel very slowly. In manufacturing a mixture of bone fiber and bone chips, two separate processes are usually required while the yield of harvested bone chips is frequently lower since they are obtained from different bone sites. Moreover, bone harvesting from different sites may also result in cross contamination.

Thus, it would be useful to develop compositions and methods of hastening and increasing bone remodeling, which avoid cross contamination, provide an increased yield of harvested bone, all in one simple process.

SUMMARY

Accordingly, an osteoinductive implantable composition comprising a mixture of demineralized bone fibers and mineralized bone fibers is provided. The mixture is visible under X ray and remodels more easily than comparable mixtures of demineralized bone matrix and surface demineralized cortical bone chips. In some embodiments, because the implantable composition uses bone fibers, it is easier to manufacture as one procedure for harvesting fibers can be used.

In some embodiments, the osteoinductive implantable compositions comprises demineralized bone fibers in an amount from about 30 vol % to about 45 vol % and mineralized bone fibers in an amount from about 55 vol % to about 70 vol %. In various embodiments, the osteoinductive implantable composition comprises, consists essentially of or consists of demineralized bone fibers in an amount from about 20 vol % to about 90 vol %, from about 30 vol % to about 80 vol %, from about 40 vol % to about 70 vol %, from about 50 vol % to about 60 vol %, the remainder comprising mineralized bone fibers. In some embodiments, the osteoinductive implantable composition comprises, consists essentially of or consists of demineralized bone fibers in an amount from about 30 vol % to about 45 vol %, the remainder comprising mineralized bone fibers.

In various embodiments, the osteoinductive implantable composition comprises, consists essentially of or consists of mineralized bone fibers in an amount from about 10 vol % to about 90 vol %, from about 20 vol % to about 80 vol %, from about 30 vol % to about 70 vol %, from about 40 vol % to about 60 vol %, from about 50 vol % to about 60 vol %, the remainder comprising demineralized bone fibers. In some embodiments, the osteoinductive implantable composition comprises, consists essentially of, or consists of mineralized bone fibers in an amount from about 55 vol % to about 70 vol %, the remainder comprising demineralized bone fibers. In other embodiments, the osteoinductive implantable composition further comprises autograft bone from about 30 vol % to about 60 vol %.

The osteoinductive implantable compositions can be delivered in delivery systems including mesh coverings for administration at surgical sites. In some embodiments the delivery system comprises at least one compartment containing the osteoinductive implantable composition disclosed herein. In these embodiments, the demineralized bone fibers may generally provide osteoinductive characteristics and the mineralized bone fibers may generally provide osteoconductive characteristics.

A method of treating a bone defect caused by injury, disease, wounds, or surgery utilizing the osteoinductive implantable composition comprising a mixture of demineralized bone fibers and mineralized bone fibers is also provided.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

Figure 1:
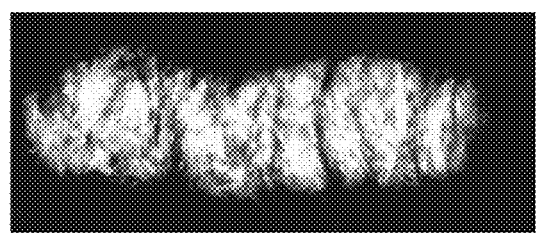
FIGS. 1 and 2 are µCT scan of mixtures of rabbit bone fibers in FIGS. 1a-1d, 2a-2e and rabbit bone fibers and rabbit bone chips in FIGS. 1e, 2f.
Figure 1:
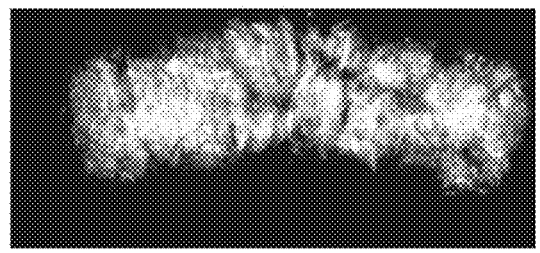
Figure 1:
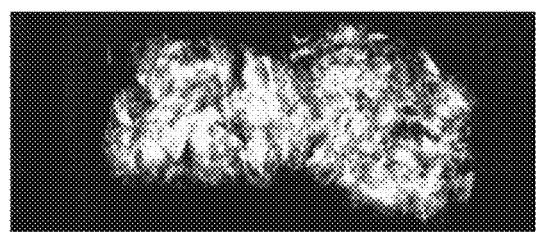
Figure 1:
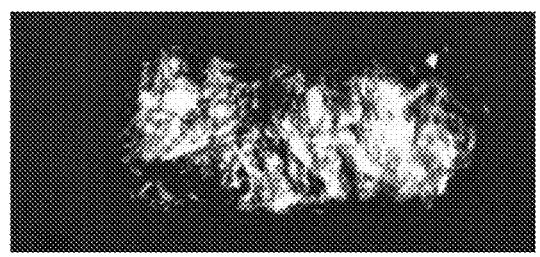
Figure 1:

It is to be understood that the figures are not shown to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

Definitions

It is noted that, as used in this specification and the appended claims, the singular forms "a," "an," and "the," include plural referents unless expressly and unequivocally limited to one referent. For example, reference to "a compartment" includes one, two, three or more compartments.

"Allograft," as used herein, refers to a graft of tissue obtained from a donor of the same species as, but with a different genetic make-up from, the recipient, as a tissue transplant between two humans.

"Bioactive agent or bioactive compound," as used herein, refers to a compound or entity that alters, inhibits, activates, or otherwise affects biological or chemical events. For example, bioactive agents may include, but are not limited to, osteogenic or chondrogenic proteins or peptides, anti-AIDS therapeutic agents, anti-cancer therapeutic agents, antibiotics, immunosuppressants, anti-viral therapeutic agents, enzyme inhibitors, hormones, neurotoxins, opioids, hypnotics, anti-histamines, lubricants, tranquilizers, anticonvulsants, muscle relaxants and anti-Parkinson therapeutic agents, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and antiadhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, anti-depressants, anti-psychotic therapeutic agents, anti-emetics, and imaging agents. In certain embodiments, the bioactive agent is a drug. Bioactive agents further include RNAs, such as siRNA, and osteoclast stimulating factors. In some embodiments, the bioactive agent may be a factor that stops, removes, or reduces the activity of bone growth inhibitors. In some embodiments, the bioactive agent is a growth factor, cytokine, extracellular matrix molecule or a fragment or derivative thereof, for example, a cell attachment sequence such as RGD. A more complete listing of bioactive agents and specific drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", Edited by Susan Budavari et al., CRC Press, 1996; and the United States Pharmacopeia-25/National Formulary-20, published by the United States Pharmcopeial Convention, Inc., Rockville Md., 2001, each of which is incorporated herein by reference.

"Biocompatible," as used herein, refers to materials that, upon administration in vivo, do not induce undesirable long-term effects.

"Bone," as used herein, refers to bone that is cortical, cancellous or cortico-cancellous of autogenous, allogenic, xenogenic, or transgenic origin.

"Demineralized," as used herein, refers to any material generated by removing mineral material from tissue, for example, bone tissue. In certain embodiments, the demineralized compositions described herein include preparations containing less than 5% calcium and preferably less than 1% calcium by weight. Partially demineralized bone (e.g., preparations with greater than 5% calcium by weight but containing less than 100% of the original starting amount of calcium) is also considered within the scope of the invention. In some embodiments, demineralized bone has less than 95% of its original mineral content. Demineralized is intended to encompass such expressions as "substantially demineralized," "partially demineralized," and "fully demineralized."

"Demineralized bone matrix," as used herein, refers to any material generated by removing mineral material from bone tissue. In preferred embodiments, the DBM compositions as used herein include preparations containing less than 5% calcium and preferably less than 1% calcium by weight. Partially demineralized bone (for example, preparations with greater than 5% calcium by weight but containing less than 100% of the original starting amount of calcium) are also considered within the scope of the invention.

"Mineralized" as used herein, refers to bone that has been subjected to a process that caused a decrease in their original organic content (e.g., de-fatting, de-greasing). Such a process can result in an increase in the relative inorganic mineral content of the bone. Mineralization may also refer to the mineralization of a matrix such as extracellular matrix or demineralized bone matrix. The mineralization process may take place either in vivo or in vitro.

"Osteoconductive," as used herein, refers to the ability of a non-osteoinductive therapeutic agent to serve as a suitable template or therapeutic agent along which bone may grow.

"Osteogenic," as used herein, refers to the ability of an agent, material, or implant to enhance or accelerate the growth of new bone tissue by one or more mechanisms such as osteogenesis, osteoconduction, and/or osteoinduction.

"Osteoimplant," as used herein, refers to any bone-derived implant prepared in accordance with the embodiments of this invention and therefore is intended to include expressions such as bone membrane, bone graft.

"Osteoinductive," as used herein, refers to the quality of being able to recruit cells from the host that have the potential to stimulate new bone formation. Any material that can induce the formation of ectopic bone in the soft tissue of an animal is considered osteoinductive. For example, most osteoinductive materials induce bone formation in athymic rats when assayed according to the method of Edwards et al., "Osteoinduction of Human Demineralized Bone: Characterization in a Rat Model," Clinical Orthopaedics & Rel. Res., 357:219-228, December 1998, incorporated herein by reference. In other instances, osteoinduction is considered to occur through cellular recruitment and induction of the recruited cells to an osteogenic phenotype. Osteoinductivity score refers to a score ranging from 0 to 4 as determined according to the method of Edwards et al. (1998) or an equivalent calibrated test. In the method of Edwards et al., a score of "0" represents no new bone formation; "1" represents 1%-25% of implant involved in new bone formation; "2" represents 26-50% of implant involved in new bone formation; "3" represents 51%-75% of implant involved in new bone formation; and "4" represents >75% of implant involved in new bone formation. In most instances, the score is assessed 28 days after implantation. However, the osteoinductivity score may be obtained at earlier time points such as 7, 14, or 21 days following implantation. Percentage of osteoinductivity refers to an osteoinductivity score at a given time point expressed as a percentage of activity, of a specified reference score.

"Remodeling" as used herein, describes the process by which native bone, processed bone allograft, whole bone sections employed as grafts, and/or other bony tissues are replaced with new cell-containing host bone tissue by the action of osteoclasts and osteoblasts. Remodeling also describes the process by which non-bony native tissue and tissue grafts are removed and replaced with new, cell-containing tissue in vivo. Remodeling also describes how inorganic materials (e.g., calcium-phosphate materials, such as β-tricalcium phosphate) is replaced with living bone.

"Superficially demineralized," as used herein, refers to bone-derived elements possessing at least about 90 weight percent of their original inorganic mineral content, the expression "partially demineralized" as used herein refers to bone-derived elements possessing from about 8 to about 90 weight percent of their original inorganic mineral content and the expression "fully demineralized" as used herein refers to bone containing less than 8% of its original mineral context. The term "patient" refers to a biological system to which a treatment can be administered. A biological system can include, for example, an individual cell, a set of cells (e.g., a cell culture), an organ, or a tissue. Additionally, the term "patient" can refer to animals, including, without limitation, humans.

"Treating" or "treatment" of a disease refers to executing a protocol, which may include administering one or more drugs to a patient (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols, which have only a marginal effect on the patient.

"Xenograft," as used herein, refers to tissue or organs from an individual of one species transplanted into or grafted onto an organism of another species, genus, or family.

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, for example, 5.5 to 10.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

The headings below are not meant to limit the disclosure in any way; embodiments under any one heading may be used in conjunction with embodiments under any other heading.

I. Introduction

Osteoinductive compositions, implants prepared therefrom and methods of treatment are provided. In various embodiments, the osteoinductive compositions provided herein comprise a mixture of demineralized bone fibers and mineralized bone fibers. The resulting mixture of demineralized bone fibers and mineralized bone fibers is easily visible on x-ray and remodels more quickly than comparable mixtures comprising human demineralized bone matrix and surface demineralized bone chips. The mineralized fibers are used to provide mechanical support, osteoconductivity, and radio-opacity. In some embodiments, because the implantable composition uses bone fibers, it is easier to manufacture as one procedure for harvesting fibers can be used as opposed to, for example, harvesting both bone chips and fibers.

II. Osteoinductive Implantable Bone Composition

Bone grafting is used to repair bone voids that are extremely complex, pose a significant health risk to the patient, or fail to heal properly. This is done with materials either from the patient's own body or by using an artificial, synthetic, or natural substitute. Demineralized bone matrix (DBM) based materials are commonly used in these procedures to substitute for, or extend the volume of, autograft and local bone.

Studies of histology slides of demineralized bone matrix and surface demineralized bone chips in a mixture of 40:60 weight percent revealed that osteimplantable compositions containing bone chips though still Xray visible do no remodel well when incorporated into a host bone even after long periods of time, as long as, for example 28 days. As a result, other mixtures were investigated and it has been unexpectedly found that mixtures of demineralized bone fibers as found in demineralized bone matrix and mineralized bone fibers remodel much more quickly as illustrated in FIGS. 1-3 described below.

Figure 2:
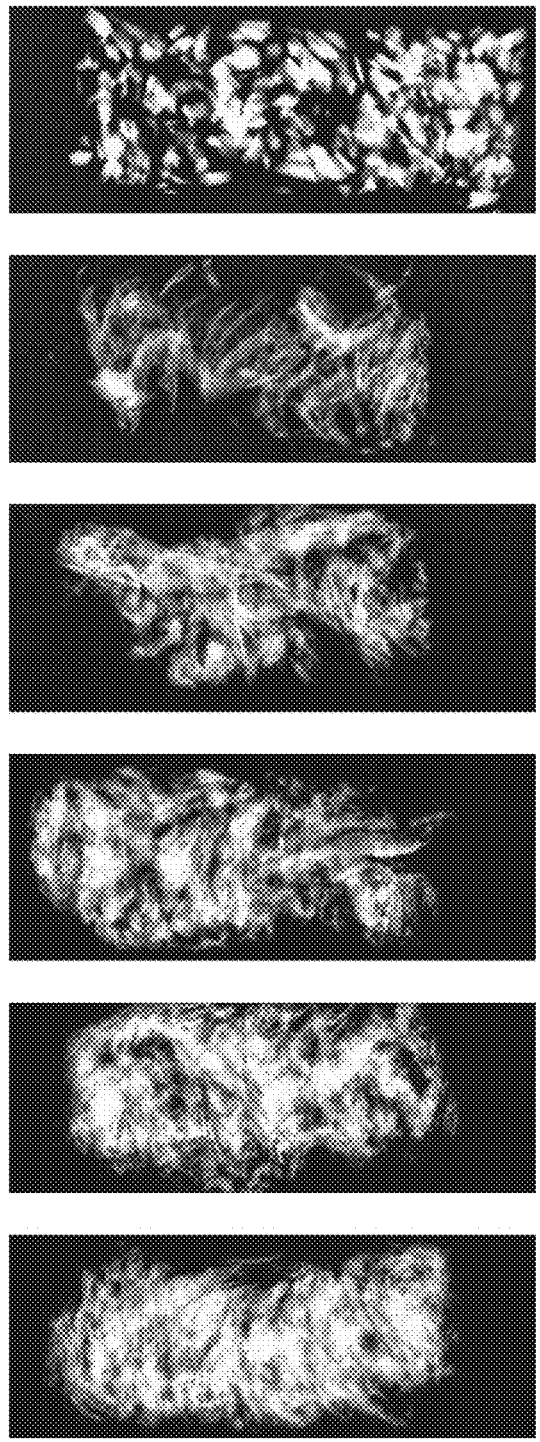
Figure 3:
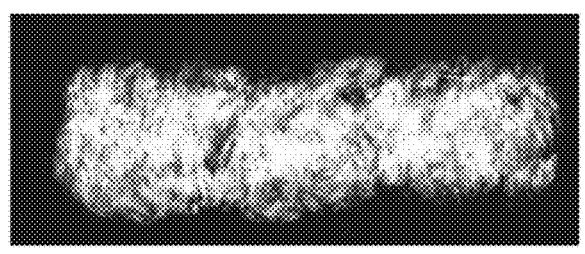
FIG. 3 is a µCT scan of mixtures of human bone fibers in FIGS. 3a-3d and rabbit bone fibers and rabbit bone chips in FIG. 3e.
Figure 3:
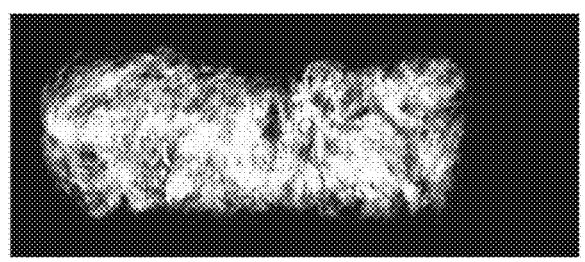
Figure 3:
Figure 3:
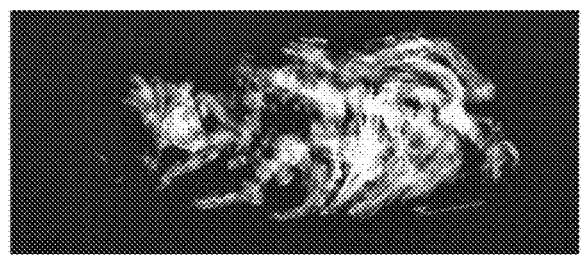
Figure 3:

FIGS. 1 and 2 are μCT scans of mixtures of demineralized rabbit bone fibers and mineralized rabbit bone fibers in various concentrations s more specifically illustrated in FIGS. 1a-1d and 2a-2e. FIGS. 1e and 2f are μCT scans of rabbit demineralized bone matrix and surface demineralized rabbit bone chips identical in composition to MagniFuse® Grafton IIeDBM, a human bone allograft, cleared by the FDA for use in extremities and in the spine under K082615. As is readily apparent from FIGS. 1e and 2f, the implant composition including bone chips does not remodel well as the bone chips appear not assimilated under the μCT scan. By contrast, the osteoimplants comprising demineralized and mineralized rabbit bone fibers illustrated in FIGS. 1a-1d and 2a-2d exhibit significantly better integration, indicative of increased remodeling characteristics.

Similar results have been observed for osteoimplant compositions containing mixtures of demineralized and mineralized human bone fibers. Specifically, FIGS. 3a-3d are μCT scans of various concentrations of demineralized/mineralized human bone fibers. FIG. 3e is a μCT scan of demineralized human bone matrix and surface demineralized bone chips as found in MagniFuse® Grafton IIeDBM. In FIG. 3e, the bone chips are still visible indicating that remodeling has not occurred to an appreciable extent. By contrast, the osteoimplants comprising demineralized and mineralized human bone fibers illustrated in FIGS. 3a-3d exhibit significantly better integration, indicative of increased remodeling characteristics.

Figure 4:
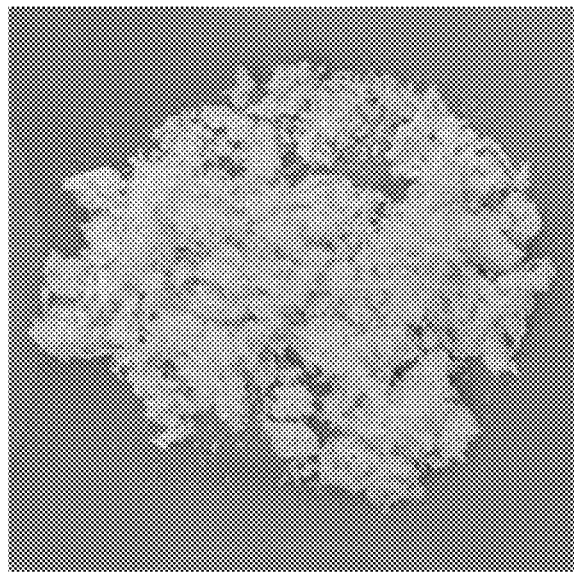
FIG. 4 illustrates µCT scan of human cartridge milled mineralized fiber in FIG. 4a and rabbit cartridge milled mineralized fiber.
Figure 4:
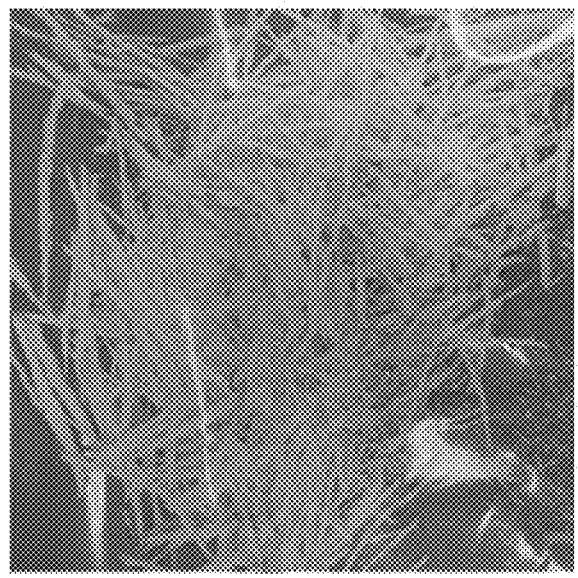

FIG. 4 illustrates human cartridge milled mineralized bone in FIG. 4a and rabbit cartridge milled mineralized bone in FIG. 4b. the human mineralized bone fiber are larger than the rabbit ones and are expected to participate in remodeling more effectively.

Figure 5:
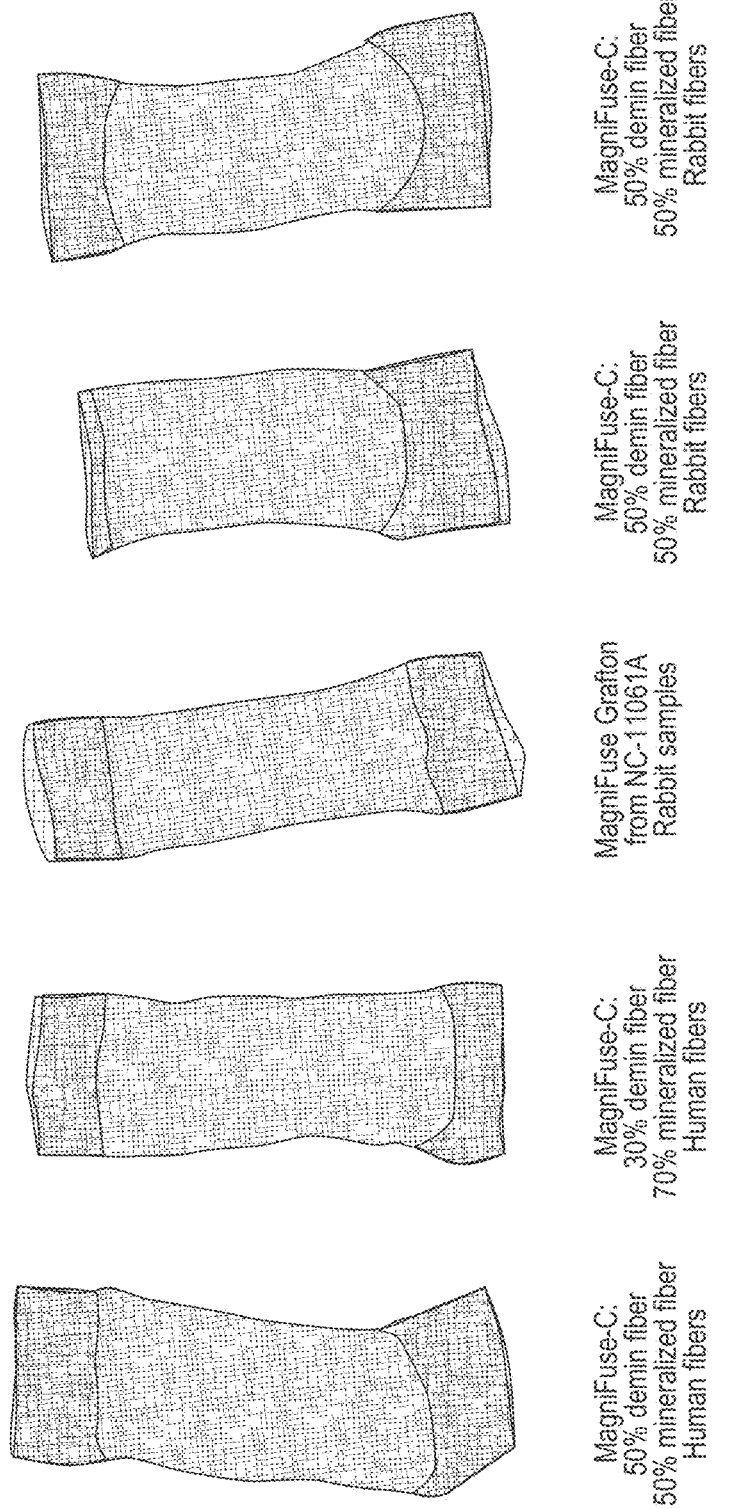
FIG. 5 illustrates mixtures of human bone fibers in FIGS. 5a, 5b and rabbit bone fibers in FIGS. 5d, 5e with a rabbit sample of MagniFuse® Grafton IIeDBM in FIG. 5c.

Finally, in FIG. 5, various mixtures of demineralized/mineralized human (FIGS. 5a, 5b) and rabbit (FIGS. 5d, 5e) bone fibers in various concentrations are enclosed in mesh coverings. FIG. 5c illustrates a sample of rabbit MagniFuse® Grafton IIeDBM containing surface demineralized bone chips enclosed in a mesh bone covering.

In various embodiments, the osteoinductive implantable composition comprises, consists essentially of or consists of demineralized bone fibers in an amount from about 20 vol % to about 90 vol %, from about 30 vol % to about 80 vol %, from about 40 vol % to about 70 vol %, from about 50 vol % to about 60 vol %, the remainder comprising mineralized bone fibers. In some embodiments, the osteoinductive implantable composition comprises, consists essentially of or consists of demineralized bone fibers in an amount from about 30 vol % to about 45 vol %, the remainder comprising mineralized bone fibers.

In various embodiments, the osteoinductive implantable composition comprises, consists essentially of or consists of mineralized bone fibers in an amount from about 10 vol % to about 90 vol %, from about 20 vol % to about 80 vol %, from about 30 vol % to about 70 vol %, from about 40 vol % to about 60 vol %, from about 50 vol % to about 60 vol %, the remainder comprising demineralized bone fibers. In some embodiments, the osteoinductive implantable composition comprises, consists essentially of, or consists of mineralized bone fibers in an amount from about 55 vol % to about 70 vol %, the remainder comprising demineralized bone fibers.

III. Providing Demineralized Bone

Following shaving, milling or other technique whereby they are obtained, the elongated fibers are subjected to demineralization in order to reduce their inorganic content to a very low level, in some embodiments, to not more than about 5% by weight of residual calcium and preferably to not more than about 1% by weight residual calcium. Demineralization of the elongated fibers ordinarily results in their contraction to some extent.

Demineralization of the fibers can be conducted in accordance with known conventional procedures. For example, in a preferred demineralization procedure, the fibers useful for the implantable composition of this application are subjected to an acid demineralization step that is followed by a defatting/disinfecting step. The bone is immersed in acid over time to effect its demineralization. Acids which can be employed in this step include inorganic acids such as hydrochloric acid and organic acids such as peracetic acid. After acid treatment, the bone is rinsed with sterile water for injection, buffered with a buffering agent to a final predetermined pH and then finally rinsed with water for injection to remove residual amounts of acid and buffering agent or washed with water to remove residual acid and thereby raise the pH. Following demineralization, the bone is immersed in solution to effect its defatting. A preferred defatting/disinfectant solution is an aqueous solution of ethanol, the ethanol being a good solvent for lipids and the water being a good hydrophilic carrier to enable the solution to penetrate more deeply into the bone. The aqueous ethanol solution also disinfects the bone by killing vegetative microorganisms and viruses. Ordinarily at least about 10 to 40 weight percent by weight of water (i.e., about 60 to 90 weight percent of defatting agent such as alcohol) should be present in the defatting/disinfecting solution to produce optimal lipid removal and disinfection within the shortest period of time. The preferred concentration range of the defatting solution is from about 60 to 85 weight percent alcohol and most preferably about 70 weight percent alcohol. Further in accordance with this application, the demineralized bone fibers can be used immediately for preparation of the implant composition or they can be stored under aseptic conditions, advantageously in a lyophilized state prior to such preparation. In a preferred embodiment, the fibrous bone elements can retain some of their original mineral content such that the composition is rendered capable of being imaged utilizing radiographic techniques.

In one embodiment, the demineralized bone is sourced from bovine or human bone. In another embodiment, demineralized bone is sourced from human bone. In one embodiment, the demineralized bone is sourced from the patient's own bone (autogenous bone). In another embodiment, the demineralized bone is sourced from a different animal (including a cadaver) of the same species (allograft bone).

Demineralized Bone Matrix

In various embodiments, this application also provides bone matrix compositions and, more specifically, bone matrix compositions including demineralized bone fibers having an average length greater than at least 0.5 cm. In various embodiments, the average length of the demineralized bone fibers is from about 0.5 cm to about 9 cm. In various embodiments, the aspect ratio of the demineralized bone fibers is from about 50:1 to about 1000:1, from about 50:1 to about 950:1, from about 50:1 to about 750:1, from about 50:1 to about 500:1, from about 50:1 to about 250:1, from about 50:1 to about 100:1, from about 10:1 to about 50:1, or from about 5:1 to about 10:1.

To prepare the osteogenic composition utilizing the fibers described herein, a quantity of fibers is combined with a biocompatible carrier to provide a demineralized bone matrix.

Carrier

Generally, materials for the carrier may be biocompatible in vivo and optionally biodegradable. In some uses, the carrier acts as a temporary scaffold until replaced completely by new bone. Suitable carriers can be any number of compounds and/or polymers, such as polymer sugars, proteins, long chain hydrophilic block copolymers, reverse phase block copolymers, hyaluronic acid, polyuronic acid, mucopolysaccharide, proteoglycan, polyoxyethylene, surfactants, including the pluronics series of nonionic surfactants, and peptide thickener. Suggested classes of biocompatible fluid carrier would include polyhydroxy compound, polyhydroxy ester, fatty alcohol, fatty alcohol ester, fatty acid, fatty acid ester, liquid silicone, mixtures thereof, and the like. Settable materials may be used, and they may set up either in situ, or prior to implantation. The bone fibers and carrier (or delivery or support system) together form an osteoimplant useful in clinical applications.

Examples of suitable biocompatible fluid carrier include, but are not limited to:

(i) Polyhydroxy compound, for example, such classes of compounds as the acyclic polyhydric alcohols, non-reducing sugars, sugar alcohols, sugar acids, monosaccharides, disaccharides, water-soluble or water dispersible oligosaccharides, polysaccharides and known derivatives of the foregoing. Specific polyhydroxy compounds include, 1,2-propanediol, glycerol, 1,4,-butylene glycol trimethylolethane, trimethylolpropane, erythritol, pentaerythritol, ethylene glycols, diethylene glycol, triethylene glycol, tetraethylene glycol, propylene glycol, dipropylene glycol; polyoxyethylene-polyoxypropylene copolymer, for example, of the type known and commercially available under the trade names Pluronic and Emkalyx; polyoxyethylene-polyoxypropylene block copolymer, for example, of the type known and commercially available under the trade name Poloxamer; alkylphenolhydroxypolyoxyethylene, for example, of the type known and commercially available under the trade name Triton, polyoxyalkylene glycols such as the polyethylene glycols, xylitol, sorbitol, mannitol, dulcitol, arabinose, xylose, ribose, adonitol, arabitol, inositol, fructose, galactose, glucose, mannose, sorbose, sucrose, maltose, lactose, maltitol, lactitol, stachyose, maltopentaose, cyclomaltohexaose, carrageenan, agar, dextran, alginic acid, guar gum, gum tragacanth, locust bean gum, gum arabic, xanthan gum, amylose, mixtures of any of the foregoing, and the like.

(ii) Polyhydroxy ester, for example, liquid and solid monoesters and diesters of glycerol can be used to good effect, the solid esters being dissolved up in a suitable vehicle, for example, propylene glycol, glycerol, polyethylene glycol of 200-1000 molecular weight. Liquid glycerol esters include monacetin and diacetin and solid glycerol esters include such fatty acid monoesters of glycerol as glycerol monolaurate, glyceryl monopalmitate, glyceryl monostearate. In various embodiments, the carrier herein comprises glyceryl monolaurate dissolved in glycerol or a 4:1 to 1:4 weight mixtures of glycerol and propylene glycol, poly (oxyalkylene) glycol ester, and the like.

(iii) Fatty alcohol, for example primary alcohols, usually straight chain having from 6 to 13 carbon atoms, including caproic alcohol, caprylic alcohol, undecyl alcohol, lauryl alcohol, and tridecanol.

(iv) Fatty alcohol ester, for example, ethyl hexyl palmitate, isodecyl neopentate, octadodecyl benzoate, diethyl hexyl maleate, and the like.

(v) Fatty acid having from 6 to 11 carbon atoms, for example, hexanoic acid, heptanoic acid, octanoic acid, decanoic acid and undecanoic acid.

(vi) Fatty acid ester, for example, polyoxyethylene-sorbitan-fatty acid esters, for example, mono- and tri-lauryl, palmityl, stearyl, and oleyl esters including of the type available under the trade name Tween from Imperial Chemical Industries; polyoxyethylene fatty acid esters including polyoxyethylene stearic acid esters of the type known and commercially available under the trade name Myrj; propylene glycol mono- and di-fatty acid esters such as propylene glycol dicaprylate; propylene glycol dilaurate, propylene glycol hydroxy stearate, propylene glycol isostearate, propylene glycol laureate, propylene glycol ricinoleate, propylene glycol stearate, and propylene glycol caprylic-capric acid diester available under the trade name Miglyol; mono-, di-, and mono/di-glycerides, such as the esterification products of caprylic or caproic acid with glycerol, for example, of the type known and commercially available under the trade name lmwitor; sorbitan fatty acid esters, or of the type known and commercially available under the trade name Span, including sorbitan-monolauryl,-monopalmityl, -monostearyl, -tristearyl, -monooleyl and triolcylesters; monoglycerides, for example, glycerol monooleate, glycerol monopalmitate and glycerol monostearate, for example as known and commercially available under the trade names Myvatex, Myvaplex and Myverol, and acetylated, for example, mono- and di-acetylated monoglycerides, for example, as known and commercially available under the trade name Myvacet; isobutyl tallowate, n-butylstearate, n-butyl oleate, and n-propyl oleate.

(vii) Liquid silicone, for example, polyalkyl siloxanes such as polymethyl siloxane and poly (dimethyl siloxane) and polyalkyl arylsiloxane.

In some embodiments of the implantable composition of this application, the liquid carrier is a liquid polyhydroxy compound, liquid polyhydroxy compound derivative, liquid solution of solid polyhydroxy compound, liquid solution of solid polyhydroxy compound derivative or mixtures thereof. If necessary or desirable, in some embodiments, the liquid carrier can be dissolved or diluted with an appropriate solvent such that when combined with the elongated demineralized bone fibers described herein a composition capable of being shaped or packed into a coherent mass which retains its shape and volume over the relatively long term, until the bone formation and remodeling process is completed, is provided. Thus, the polyhydroxy compound or polyhydroxy derivatives can be a liquid in the pure or highly concentrated state at ambient temperature, from about 15° C. to about 50° C., or it can be a solid or semi-solid at this temperature in which case it becomes necessary to dissolve the material in a solvent such as water, physiological saline, ethanol, glycerol, glucose, propylene glycol, polyethylene glycol of from 200-1000 molecular weight, or polyvinyl alcohol. In other embodiments, the liquid carrier can be made up of one or more liquid polyhydroxy compounds or derivatives in solution with one or more solid polyhdroxy compounds or derivatives.

The osteoinductive or biologically active composition may be configured to be moldable, extrudable, or substantially solid. The osteoinductive or biologically active composition may be configured to substantially retain its shape in water for a period of time. The osteoinductive or biologically active composition may form an osteoimplant useful in clinical applications. Suitable carriers may include surface demineralized bone; mineralized bone; nondemineralized cancellous scaffolds; demineralized cancellous scaffolds; cancellous chips; particulate, demineralized, guanidine extracted, species-specific (allogenic) bone; specially treated particulate, protein extracted, demineralized, xenogenic bone; collagen; synthetic hydroxyapatites; synthetic calcium phosphate materials; tricalcium phosphate, sintered hydroxyapatite, settable hydroxyapatite; polylactide polymers; polyglycolide polymers, polylactide-co-glycolide copolymers; tyrosine polycarbonate; calcium sulfate; collagen sheets; settable calcium phosphate; polymeric cements; settable poly vinyl alcohols, polyurethanes; resorbable polymers; and other large polymers; liquid settable polymers; and other biocompatible settable materials. The carrier may further comprise a polyol (including glycerol or other polyhydroxy compound), a polysaccharide (including starches), a hydrogel (including alginate, chitosan, dextran, pluronics, N,O-carboxymethylchitosan glucosamine (NOCC)), hydrolyzed cellulose, or a polymer (including polyethylene glycol). In embodiments wherein chitosan is used as a carrier, the chitosan may be dissolved using known methods including in water, in mildly acidic aqueous solutions, in acidic solutions.

The carrier may further comprise a hydrogel such as hyaluronic acid, dextran, pluronic block copolymers of polyethylene oxide and polypropylene, and others. Suitable polyhydroxy compounds include such classes of compounds as acyclic polyhydric alcohols, non-reducing sugars, sugar alcohols, sugar acids, monosaccharides, disaccharides, water-soluble or water dispersible oligosaccharides, polysaccharides and known derivatives of the foregoing. An example carrier comprises glyceryl monolaurate dissolved in glycerol or a 4:1 to 1:4 weight mixture of glycerol and propylene glycol. Settable materials may be used, and they may set up either in situ, or prior to implantation. Optionally, xenogenic bone powder carriers also may be treated with proteases such as trypsin. Xenogenic carriers may be treated with one or more fibril modifying agents to increase the intraparticle intrusion volume (porosity) and surface area. Useful agents include solvents such as dichloromethane, trichloroacetic acid, acetonitrile and acids such as trifluoroacetic acid and hydrogen fluoride. The choice of carrier may depend on the desired characteristics of the composition. In some embodiments, a lubricant, such as water, glycerol, or polyethylene glycol may be added.

Any suitable shape, size, and porosity of carrier may be used. In some embodiments, the carrier may be settable and/or injectable. Such carrier may be, for example, a polymeric cement, a suitable settable calcium phosphate, a settable poly vinyl alcohol, a polyurethane, or a liquid settable polymer. Hydrogel carriers may additionally impart improved spatial properties, such as handling and packing properties, to the osteoconductive composition. An injectable carrier may be desirable where the composition is used with a containment device. In addition, selected materials must be biocompatible in vivo and optionally biodegradable. In some uses, the carrier acts as a temporary scaffold until replaced by new bone. Polylactic acid (PLA), polyglycolic acid (PGA), and various combinations have different dissolution rates in vivo. In bone, the dissolution rates can vary according to whether the composition is placed in cortical or trabecular bone.

In certain embodiments, the carrier may comprise a shape-retaining solid made of loosely adhered particulate material with collagen. It may alternatively comprise a molded, porous solid, a monolithic solid, or an aggregate of close-packed particles held in place by surrounding tissue. Masticated muscle or other tissue may also be used. Large allogenic bone implants may act as a carrier, for example where their marrow cavities are cleaned and packed with DBM and, optionally, the osteoinductive factors.

In various embodiments, the carrier comprises an osteoinductive material such as a mineralized particulated material, osteoinductive growth factors, or partially demineralized bone. The mineralized particulated material may be TCP, hydroxyapatite, mineral recovered from bones, surface demineralized bone fiber, or other material. The osteoinductive material may be combined with a further carrier such as starch or glycerol. Accordingly, in some embodiments, the bone matrix may act as a carrier for the tissue-derived extract.

Where, in a particular implantable composition, the fibrous elements exhibit a tendency to quickly or prematurely separate from the carrier component or to otherwise settle out from the composition such that application of a fairly homogeneous composition is rendered difficult or inconvenient, it can be advantageous to include within the composition an optional substance whose thixotropic characteristics prevent or reduce this tendency. Thus, for example, where the carrier component is glycerol and separation of fibrous and/or non-fibrous bone elements occurs to an excessive extent where a particular application is concerned, a thixotropic agent such as a solution of polyvinyl alcohol, polyvinylpyrrolidone, cellulosic ester such as hydroxypropyl methylcellulose, carboxylmethylcellulose, pectin, food-grade texturizing agent, gelatin, dextran, collagen, starch, hydrolyzed polyacrylonitrile, hydrolyzed polyacrylamide, polyelectrolyte such as polyacrylic acid salt, hydrogels, chitosan, other materials that can suspend the fibrous elements, can be combined with the carrier in an amount sufficient to significantly improve the suspension-keeping characteristics of the composition.

In some embodiments when the fibers are elongated, for example from 2.0 cm to about 9 cm, they often interlock and become densely entangled. Although not bound by any particular theory or mode of operation, it is believed that the ability of the elongated fibers to interlock and become entangled with each other is advantageous to the formation of coherent and cohesive DBM compositions. In various embodiments, the fibers may be combed using standard fiber combing techniques known in the art to reduce entanglement in order to obtain elongated fibers which are lightly entangled and as a result are less cohesive.

Preparation of DBM Composition

To prepare a DBM composition according to one or more embodiments of this application, a quantity of demineralized bone fibers prepared as described above is combined with water or any other appropriate, biocompatible liquid to form a smooth, flowable, cohesive paste. The resultant implantable composition may be molded or injected into any desired shape and retains its shape, even when submersed in water, saline, or other aqueous solution. An additional benefit of the DBM fibers is that the resultant paste is injectable through an 18-gauge needle.

The liquid may be any biocompatible liquid, including water, saline solution, buffered solutions, serum, bone marrow aspirant, blood, platelet-rich plasma and the like and mixtures thereof. Some biocompatible liquids suitable for use with the DBM fibers, such as serum, bone marrow aspirant and blood, additionally contain osteoinductive factors that will promote bone growth at the site to which the composition is applied.

Optional Additives

If desired, the fibrous bone elements of this application can be modified in one or more ways. In various embodiments, any of a variety of medically and/or surgically useful optional substances can be incorporated in, or associated with, the bone elements before, during, or after preparation of the implantable composition. Thus, in some embodiments, one or more of such substances can be introduced into the bone elements, for example, by soaking or immersing the bone elements in a solution or dispersion of the desired substance(s), by adding the substance(s) to the carrier component of the implantable composition or by adding the substance(s) directly to the implantable composition.

Medically/surgically or bioactively useful substances which can be readily combined with the demineralized bone fibers, fluid carrier and/or implantable composition of this application include, for example, collagen, insoluble collagen derivatives, hydroxyapatite, and soluble solids and/or liquids dissolved therein, for example, antiviricides, particularly those effective against HIV and hepatitis; antimicrobials and/or antibiotics such as erythromycin, bacitracin, neomycin, penicillin, polymyxin B, tetracyclines, viomycin, chloromycetin and streptomycins, cefazolin, ampicillin, azactam, tobramycin, clindamycin and gentamycin; amino acids, peptides, vitamins, inorganic elements, inorganic compounds, cofactors for protein synthesis, hormones; endocrine tissue or tissue fragments; synthesizers; enzymes such as collagenase, peptidases, oxidases; polymer cell scaffolds with paraenchymal cells; angiogenic drugs and polymeric carriers containing such drugs; collagen lattices; biocompatible surface active agents; antigenic agents; cytoskeletal agents; cartilage fragments, living cells such as chondrocytes, bone marrow cells, mesenchymal stem cells, natural extracts, tissue transplants, bioadhesives, bone morphogenic proteins (BMPs), transforming growth factor (TGF-beta), insulin-like growth factor (IGF-1) (IGF-2), platelet derived growth factor (PDGF), fibroblast growth factors (FGF), vascular endothelial growth factor (VEGF), angiogenic agents, bone promoters, cytokines, interleukins, genetic material, genes encoding bone promoting action, cells containing genes encoding bone promoting action; growth hormones such as somatotropin; bone digestors; antitumor agents; fibronectin; cellular attractants and attachment agents; immuno-suppressants; permeation enhancers, for example, fatty acid esters such as laureate, myristate and stearate monesters of polyethylene glycol, surface active agents, enamine derivatives, α-keto aldehydes; nucleic acids; epidermal growth factor (EGF); all collagen types (not just type 1); non-collagenous proteins such as osteopontin, osteonectine, bone sialo proteins, vitronectin, thrombospondin, proteoglycans, decorin, biglycan, aggrecan, versican, tenascin, matrix gla protein hyaluronan; soluble and insoluble components of the immune system, soluble and insoluble receptors including truncated forms, soluble, insoluble and cell surface bound ligands including truncated forms; chemokines, bioactive compounds that are endocytosed; compounds capable of altering the membrane potential of cells, compounds capable of altering the monovalent and divalent cation/anion channels of cells; bone resorption inhibitors and stimulators; angiogenic and mitogenic factors; bioactive factors that inhibit and stimulate second messenger molecules; integrin adhesion molecules; clotting factors; externally expanded autograft or xenograft cells and any combinations thereof. The amounts of such optionally added substances can vary widely with optimum levels being readily determined in a specific case by routine experimentation. In certain embodiments, the bioactive agent may be a drug. In some embodiments, the bioactive agent may be a growth factor, cytokine, extracellular matrix molecule, or a fragment or derivative thereof, for example, a protein or peptide sequence such as RGD.

The demineralized bone matrix prepared with demineralized bone fibers may comprise a number of materials in combination, some or all of which may be in the form of fibers and/or particles. The matrix may comprise calcium phosphates. Driessens et al. "Calcium phosphate bone cements," Wise, D. L., Ed., Encyclopedic Handbook of Biomaterials and Bioengineering, Part B, Applications New York: Marcel Decker; Elliott, Structure and Chemistry of the Apatites and Other Calcium Phosphates Elsevier, Amsterdam, 1994, each of which is incorporated by reference. Calcium phosphate matrices include, but are not limited to, dicalcium phosphate dihydrate, monetite, tricalcium phosphate, tetracalcium phosphate, hydroxyapatite, nanocrystalline hydroxyapatite, poorly crystalline hydroxyapatite, substituted hydroxyapatite, and calcium deficient hydroxyapatites. In some embodiments, the bone fibers may be added to a carrier.

Implantable DBM compositions have been used for many years in orthopedic medicine to promote the formation of bone. For example, DBM compositions have found use in the repair of fractures, in the fusion of vertebrae, in joint replacement surgery, and in treating bone destruction due to underlying disease such as rheumatoid arthritis. DBM is thought to promote bone formation in vivo by osteoconductive and osteoinductive processes. The osteoinductive effect of implanted DBM compositions is thought to result from the presence of active growth factors present on the isolated collagen-based matrix. These factors include members of the TGF-β, IGF, and BMP protein families. Particular examples of osteoinductive factors include TGF-β, IGF-1, IGF-2, BMP-2, BMP-7, parathyroid hormone (PTH), and angiogenic factors. Other osteoinductive factors such as osteocalcin and osteopontin are also likely to be present in DBM preparations as well. There are also likely to be other unnamed or undiscovered osteoinductive factors present in DBM.

In some embodiments, the demineralized bone may be further treated to affect properties of the bone. For example, the DBM may be treated to disrupt the collagen structure of the DBM. Such treatment may comprise collagenase treatment, heat treatment, mechanical treatment, or other. While demineralized bone is specifically discussed herein, in some embodiments, the teachings herein may be applied to non-demineralized bone, to partially demineralized bone, or to surface demineralized bone.

In some embodiments, biological activities of the demineralized bone matrix may be increased. Accordingly, the demineralized bone matrix, and compositions formed from the demineralized bone matrix, may variously be referred to as biologically active and/or, in some cases, osteoinductive. The biological activities of the bone composition provided herein that may be increased include but are not limited to osteoinductive activity, osteogenic activity, chondrogenic activity, wound healing activity, neurogenic activity, contraction-inducing activity, mitosis-inducing activity, differentiation-inducing activity, chemotactic activity, angiogenic or vasculogenic activity, exocytosis or endocytosis-inducing activity, or other cell or biological activity. It will be appreciated that bone formation processes frequently include a first stage of cartilage formation that creates the basic shape of the bone, which then becomes mineralized (endochondral bone formation). Thus, in many instances, chondrogenesis may be considered an early stage of osteogenesis, though of course it may also occur in other contexts.

In accordance with various embodiments, the demineralized bone matrix provided herein may be used with growth factors, extracts, peptide hormones, or other additives to increase the osteoinductive capacity or that otherwise encourage cell or biological activity of the bone matrix or to impart other benefits to the bone matrix. It will be appreciated that the amount of additive used will vary depending upon the type of additive, the specific activity of the particular additive preparation employed, and the intended use of the composition. The desired amount is readily determinable by the user.

Any of a variety of medically and/or surgically useful optional substances can be incorporated in, or associated with, the osteoinductive factors either before, during, or after preparation of the osteoinductive or biologically active composition. Thus, for example when demineralized bone fibers of this application are used to form the material, one or more of such substances may be introduced into the demineralized bone fibers, for example, by soaking or immersing these bone fibers in a solution or dispersion of the desired substance(s).

In one embodiment, a tissue-derived extract may be added to the bone matrix. U.S. patent application Ser. No. 12/140,044 discloses such extracts and addition of such extracts to DBM and is incorporated herein by reference. For example, a tissue-derived extract or partially demineralized bone may be added to the bone matrix. The extract may be derived from any suitable tissue, such as bone, bladder, kidney, brain, skin, or connective tissue. Further, the extract may be derived in any suitable manner. The extract may be allogeneic, autogeneic, xenogeneic, or transgenic. In embodiments wherein the extract is bone-derived, the bone may be cortical, cancellous, or corticocancellous and may be demineralized, partially demineralized, or mineralized. In some embodiments, the extract may comprise demineralized bone, partially demineralized bone, mineral derived from bone, or collagen derived from bone. In some embodiments, the tissue-derived extract may be a protein extract.

Bone regeneration involves a multitude of cells, for example, cartilage, fibroblasts, endothelial cells besides osteoblasts. Accordingly, the demineralized bone matrix composition may be used to deliver stem cells, which offers the potential to give rise to different types of cells in the bone repair process. In one embodiment, the demineralized bone matrix composition further comprises a cell such as an osteogenic cell or a stem cell.

In various embodiments, the additive may comprise radiopaque substances, angiogenesis promoting materials, bioactive agents, osteoinducing agents, or other. Such materials would include without limitation barium sulfate, iodine-containing compounds, titanium and mineralized bone.

In certain embodiments, the additive is adsorbed to or otherwise associated with the demineralized bone matrix. The additive may be associated with the demineralized bone matrix through specific or non-specific interactions, or covalent or noncovalent interactions. Examples of specific interactions include those between a ligand and a receptor, an epitope or an antibody. Examples of nonspecific interactions include hydrophobic interactions, electrostatic interactions, magnetic interactions, dipole interactions, van der Waals interactions, or hydrogen bonding. In certain embodiments, the additive is attached to the demineralized bone matrix composition, for example, to the carrier, using a linker so that the additive is free to associate with its receptor or site of action in vivo. In other embodiments the additive is either covalently or non-covalently attached to the carrier. In certain embodiments, the additive may be attached to a chemical compound such as a peptide that is recognized by the carrier. In another embodiment, the additive is attached to an antibody, or fragment thereof, that recognizes an epitope found within the carrier. In certain embodiments at least additives are attached to the osteoimplant. In other embodiments at least three additives are attached to the osteoinductive or biologically active composition. An additive may be provided within the osteoinductive or biologically active composition in a sustained release format. For example, the additive may be encapsulated within biodegradable polymer nanospheres, or microspheres.

Flow additives according to this application can include, but are not limited to, small molecule organic compounds, polymeric/oligomeric materials, and solutions thereof. In some embodiments, when added to the implantable composition containing the demineralized bone fibers the viscosity thereof should be sufficiently changed to allow flow through a syringe needle of about 8-gauge or greater (greater number gauges of syringe needles have smaller diameters, thus requiring lower threshold viscosity through which they may flow), preferably of about 12-gauge or greater, for example of about 14-gauge or greater, of about 15-gauge or greater, or of about 18-gauge or greater. Sufficient flow can be understood, in terms of syringe needles, to result in an injection force of not more than 50 pounds, preferably not more than 40 pounds. In another embodiment, the flow additive modifies the viscosity of the composition to which it is added such that the composition is capable of flowing through a syringe needle having a gauge size from about 8 to about 18, alternately from about 8 to about 15, from about 12 to about 18, or from about 12 to about 15.

When present, the amount of flow additive that can be added to the composition can be from about 0.01% to about 1.5% by weight of the elongated fiber composition from about 0.1% to about 1% by weight, or from about 0.05% to about 1% by weight. In an alternate embodiment, the amount of flow additive can be from about 1.5% to about 5% by weight of the elongated fiber composition. In a preferred embodiment, the flow additive, when used, is present in an amount of about 0.5% by weight of the composition.

Suitable examples of flow additives can include, but are in no way limited to, hyaluronic acid; hyaluronate salts such as sodium, potassium, lithium, or the like, or a combination thereof; alginate salts such as sodium, potassium, lithium, or the like; starch compounds, which can be present in its natural form, in a destructured form, or in any number of chemically modified derivative forms (for example, alkyoxylated derivatives, esterified derivatives, ionically modified starches, oxidized starches, grafted starches, crosslinked starches, or the like, or mixtures thereof); saturated, monounsaturated, and/or polyunsaturated oils, such as those extracted or isolated from plant and/or animal sources, including, but not limited to, sunflower, safflower, peanut, castor bean, sesame, coconut, soybean, corn, canola, olive, vegetable, palmitins, stearins, oleins, and the like, or derivatives or combinations thereof, as naturally extracted, as synthesized, or as modified or processed in some way, partially or fully hydrogenated, partially or fully dehydrogenated, partially or fully saponified, partially or fully acidified, partially halogenated, or the like; a wax including, but not limited to, hydrocarbon waxes (for example, polyolefin waxes, such as polyethylene wax, polypropylene wax, and the like, or copolymers thereof), oligoester waxes, monoester waxes, oligoether waxes, monoether waxes, and the like, or combinations thereof, as naturally extracted, as synthesized, or as modified or processed in some way, partially or fully hydrogenated, partially or fully dehydrogenated, partially or fully saponified, partially or fully acidified, partially halogenated, or the like; cellulosic compounds, including, but not limited to, native or synthetic cellulose, cotton, regenerated cellulose (for example, rayon, cellophane, or the like), cellulose acetate, cellulose propionate, cellulose butyrate, cellulose acetate-propionate, cellulose acetate-butyrate, cellulose propionate-butyrate, cellulose nitrate, methyl cellulose, ethyl cellulose, carboxymethyl cellulose, carboxyethyl cellulose, cellulose salts, and combinations or copolymers thereof, as naturally extracted, as synthesized, or as modified or processed in some way, including partially or fully esterified, partially or fully nitrated, partially or fully regenerated, partially or fully etherified, partially or fully acidified, partially or fully acid-neutralized, or the like, or combinations thereof; surface-active biomolecules or (co)polymers; poly(ethylene glycol) and/or poly(ethylene oxide) oligomers, homopolymers, or copolymers; autologous substances such as autologous bone marrow aspirates, autologous blood substances, or the like, or a combination thereof; heterologous substances such as allogeneic bone marrow aspirates, xenogenic bone marrow aspirates, allogeneic blood substances, xenogenic blood substances, or the like, or a combination thereof; or the like, or combinations thereof. In a preferred embodiment, the flow additive comprises hyaluronic acid and/or a hyaluronate salt. In another preferred embodiment, the flow additive comprises sodium hyaluronate. In an alternate embodiment, the flow additive can include chondroitin, glucosamine, hyaluronic acid, a salt thereof, or a mixture thereof.

In one or more embodiments, an additive is included in the DBM composition to further modify the handling characteristics of the composition, such as viscosity and moldability. The additive may be a biocompatible polymer, such as a water-soluble cellulosic, or a natural polymer, such as gelatin. The additive may be added to either the dry DBM component or the liquid component. The additive may be used to at least partially coat the DBM fibers prior to combining them with the liquid carrier. Non-limiting examples of additives suitable for use in the DBM composition include gelatin, carboxymethyl cellulose, hydroxypropyl methylcellulose, methylcellulose, hydroxyethyl cellulose, other cellulose derivatives, alginate, hyaluronic acid, sodium salts, polyvinyl pyrrolidones, polyvinyl alcohol, arabic gum, guar gum, xantham gum, chitosans, and poloxamers.

As previously indicated, the implantable composition of this disclosure can be freshly prepared just by mixing desired quantities of the demineralized bone fibers, mineralized bone fibers, fluid carrier and optional component(s), if any, in any suitable sequence of separate mixing, adsorption, rehydration or drying operations or all at once. Thus, the demineralized bone fibers can be mixed with the optional ingredients(s) and thereafter combined with the fluid carrier component, the demineralized bone fibers can be mixed with the fluid carrier followed by addition of the optional ingredient(s) or the optional ingredients can be added to the fluid carrier followed by addition of the demineralized bone fibers. In some embodiments, the implantable composition disclosed herein also comprises autograft. Variations of these and other sequences of mixing are, of course, possible. In various embodiments, the implantable composition can include non-fibrous bone elements. In other embodiments, the demineralized and mineralized fibers and fluid carrier are mixed substantially simultaneously such that the fibers of the implantable composition are entangled and are thoroughly mixed with each other.

In various embodiments, the demineralized bone fibers can include, for example, "substantially demineralized," "partially demineralized," or "fully demineralized" cortical and cancellous bone. These also include surface demineralization, where the surface of the bone construct is substantially demineralized, partially demineralized, or fully demineralized, yet the body of the bone construct is fully mineralized. In some embodiments, the covering may comprise some fully mineralized bone material. The configuration of the bone material can be obtained by milling, shaving, cutting or machining whole bone as described in for example U.S. Pat. No. 5,899,939. The entire disclosure is herein incorporated by reference into the present disclosure.

IV. Mineralized Bone Fibers

In certain embodiments, bone particles are subjected to a process that partially or totally removes their initial organic content to yield mineralized and anorganic bone particles, respectively. Different mineralization methods have been developed and are known (Hurley, et al., Milit. Med. 1957, 101-104; Kershaw, Pharm. J. 6:537, 1963; and U.S. Pat. No. 4,882,149; each of which is incorporated herein by reference). For example, a mineralization procedure can include a de-greasing step followed by a basic treatment (with ammonia or another amine) to degrade residual proteins and a water washing (U.S. Pat. Nos. 5,417,975 and 5,573,771; both of which are incorporated herein by reference). Another example of a mineralization procedure includes a defatting step where bone particles are sonicated in 70% ethanol for 1-3 hours.

The amount of demineralized bone fibers which can be incorporated into the implantable composition can vary widely with amounts from about 90% by volume, about 80% by volume, about 70% by volume, about 60% by volume, about 50% by volume, 45% by volume, about 30% by volume. In various embodiments, the amount of mineralized fibers which can be incorporated into the implantable composition can vary widely with amounts from about 10% by volume, 20% by volume, 30% by volume, 40% by volume, from 50% by volume, 55% by volume, 60% by volume to about 70% by volume.

V. Osteoimplant

The mixture of demineralized bone fibers and mineralized bone fibers as disclosed herein find use as, or in, implants, for a variety of orthopedic procedures where they participate in the bone healing/repair process through one or more mechanisms such as osteogenesis, osteoinduction and osteoconduction. The mixture of demineralized fibers and mineralized bone fibers can be used as is, or formed into a variety of product types such as a gel, putty, or sheet. The demineralized bone particles, with or without carrier, can optionally be admixed with one or more substances such as adhesives, fillers, plasticizers, flexibilizing agents, biostatic/biocidal agents, surface active agents, binding and bonding agents, and the like, prior to, during, or after shaping the particles into a desired configuration. Suitable adhesives, binding agents and bonding agents include acrylic resins, cellulosics, bioresorbable polymers such as polyesters, polycarbonates, polyarylates and polyfomarates, such as, for example, polycarbonates, tyrosine polyarylates, polyglycolides, polylactides, or glycolide-lactide copolymer. Suitable fillers include bone powder, demineralized bone powder, or hydroxyapatite. Suitable plasticizers and flexibilizing agents include liquid polyhydroxy compounds such as glycerol, monacetin, or diacetin. Suitable biostatic/biocidal agents include antibiotics, providone, or sugars. Suitable surface-active agents include the biocompatible nonionic, cationic, anionic or amphoteric surfactants. The bone particles or fibers may be combined with a polymer to form a biocomposite.

The mixture of demineralized and mineralized bone fibers may be subjected to a configuring step to form an implant. The configuring step can be employed using conventional equipment known to those skilled in the art to produce a wide variety of geometries, for example, concave or convex surfaces, stepped surfaces, cylindrical dowels, wedges, blocks, screws, and the like. Also useful are demineralized bone and other matrix preparations comprising additives or carriers such as binders, fillers, plasticizers, wetting agents, surface active agents, biostatic agents, biocidal agents, and the like. Some exemplary additives and carriers include polyhydroxy compounds, polysaccharides, glycosaminoglycan proteins, nucleic acids, polymers, polaxomers, resins, clays, calcium salts, and/or derivatives thereof.

The osteoimplant resulting from a carrier and the osteoinductive factors may assume a determined or regular form or configuration such as a sheet, plate, disk, tunnel, cone, or tube, to name but a few. Prefabricated geometry may include, but is not be limited to, a crescent apron for single site use, an I-shape to be placed between teeth for intra-bony defects, a rectangular bib for defects involving both the buccal and lingual alveolar ridges, neutralization plates, reconstructive plates, buttress plates, T-buttress plates, spoon plates, clover leaf plates, condylar plates, compression plates, bridge plates, or wave plates. Partial tubular as well as flat plates can be fabricated from the osteoimplant. Such plates may include such conformations as, for example, concave contoured, bowl shaped, or defect shaped. The osteoimplant can be machined or shaped by any suitable mechanical shaping means. Computerized modeling can provide for the intricately-shaped three-dimensional architecture of an osteoimplant custom-fitted to the bone repair site with great precision.

VI. Delivery System

In some embodiments, bone particles or fibers as disclosed herein, with or without carrier, may be provided in a covering to form a delivery system.

U.S. patent application Ser. No. 12/205,539 for Delivery System Attachment discloses suitable coverings for use with demineralized fibers as provided herein to form a delivery system and is herein incorporated by reference in its entirety. Accordingly, in some embodiments, a delivery system is provided comprising a covering and demineralized and mineralized bone fibers provided within the covering for delivery to the surgical site. Generally, the covering may be a single or multi-compartment structure capable of at least partially retaining a substance provided therein until the covering is placed at a surgical site. The covering may participate in, control, or otherwise adjust, the release of materials from the mixture of demineralized and mineralized bone fibers or penetration of the covering by surrounding materials, such as cells or tissues. The covering may include one or more attachment mechanisms for retaining the covering at the surgical site. The attachment mechanism may be a mechanical attachment mechanism, a physical attachment mechanism, a biological attachment mechanism or a chemical attachment mechanism, or may employ combinations of these. The attachment mechanism may be used to attach the covering to skeletal or soft tissue proximate the surgical site.

In some embodiments, the covering may be used for containment of the demineralized bone fibers and/or mineralized bone fibers. In some embodiments, the covering may be used for maintaining the demineralized bone fibers and mineralized bone fibers in spatial proximity to one another, possibly to provide a synergistic effect. In some embodiments, the delivery system may be used for delivery through a limited opening, such as in minimally invasive surgery or mini-open access.

Any suitable technique may be used for forming a material for the covering. Generally, the material may be formed as a substantially solid material, as a sheet, as a mesh, or in other configuration. In some embodiments, the material may be a textile type material. Thus, for example, the material may be formed using a textile approach such as be weaving, rug making, knitting. Such formation may be by a mechanical or industrial method. In another embodiment, a substantially solid sheet may be formed and may be treated to assume a configuration penetrable by cells, fluids, and proteins. For example, the sheet may be perforated, may be expanded to create openings, or other. Also, it would be perfectly suitable to take a thin sheet of the covering material, and to perforate it, expand it to create openings, or otherwise make it penetrable by cells, fluids and proteins.

The shape, configuration, or form of the covering may be selected for particular applications. Such shape and configuration may include, for example, the basic shape of the covering (for example, a cylinder or a bag), whether the covering has a single or a plurality of compartments, and whether the covering includes attachment mechanisms. The covering (or delivery system) may be configured to conform to surrounding bony contours of the space in which it is placed.

The covering may have any suitable configuration. For example, the covering may be formed as a ring, a cylinder, a cage, a rectangular shape, a mesh, a suture-like wrap, a continuous tube, or other configuration. In specific embodiments, the covering may be formed as a thin tube designed to be inserted through catheters or an introducer tube, a rectangular shape designed to fit adjacent to spinal processes for posterolateral spine fusion, a cube like structure designed to fit between vertebral bodies or within cages for interbody spinal fusion, a tube-like shape where the ends are designed to be fitted onto nonunion long bone defects, relatively flat shapes designed to fill cranial or maxillofacial defects, rectangular structures designed for osteochondral defects, structures pre-shaped to fit around various implants (for example, dental, doughnut with hole for dental implants), or relatively elastic ring-like structures that will stretch and then conform to shapes (for example, rubber band fitted around processes). In an embodiment wherein the covering is formed as a cage, the cage may comprise a plurality of crossed filaments which define between them a series of openings for tissue ingrowth. Any of these shapes may be used for a covering comprising a plurality of compartments. For example, in a tubular embodiment, the tube may be formed into a plurality of compartments by tying a cord around the tube at one or more points, or by other suitable mechanism such as crimping, twisting, knotting, stapling, sewing, or other. The configuration of the covering may be determined by the therapeutic agent to be provided within the covering. For example, if the therapeutic agent to be contained comprises fibers, the covering may be formed as strings or sutures that are wrapped around the fibers.

In some embodiments, the covering may have a modulus of elasticity in the range of about $1\times10^2$ to about $6\times10^5$ dynes/cm$^2$, or $2\times10^4$ to about $5\times10^5$ dynes/cm$^2$, or $5\times10^4$ to about $5\times10^5$ dynes/cm$^2$. After the cover is administered to the target site, the covering may have a modulus of elasticity in the range of about $1\times-10^2$ to about $6\times10^5$ dynes/cm$^2$, or $2\times10^4$ to about $5\times10^5$ dynes/cm$^2$, or $5\times10^4$ to about $5\times10^5$ dynes/cm$^2$.

In one embodiment, demineralized bone fibers may be provided in a first compartment and mineralized bone fibers may be provided in a second compartment. In this embodiment, the demineralized bone fibers may generally provide osteoinductive characteristics and the mineralized bone fibers may generally provide osteoconductive characteristics. In use, the covering may be laid flat on the transverse process and positioned such that the first compartment, holding the demineralized bone fibers, is nearest the vertebral body and the second compartment, holding the mineralized bone fibers, is farther from the vertebral body, or the compartments may be positioned in any other desired configuration. In another embodiment, a covering may comprise first and second compartments wherein autograft may be placed in one of the compartments prior to placement of the covering in vivo. In other embodiments, three or more compartments may be used, as appropriate for the materials being delivered and the application of the compartmented implant. More than one substance may be provided in a compartment. For example, mineralized bone fibers and demineralized bone fibers may be mixed and provided within a single compartment. Such mixture of substances within a single compartment may be a substantially uniform mix or may be a plurality of substances placed in the compartment separately such that they are substantially unmixed. When multiple compartments are used, each compartment may contain one or more substances. Exemplary substances that may be provided in one or more compartments of the delivery system include cells from the osteogenic precursors, growth factors, angiogenic factors and other active proteins including bone morphogenic proteins, and cellular scaffolding materials of natural or synthetic origin, antibiotics, and other substances described below.

In accordance with alternative embodiments, other delivery systems may be formed using the mixture of demineralized bone fibers and mineralized bone fibers disclosed herein. In one embodiment, a plurality of thin sheets are provided. Each sheet comprises a carrier admixed with demineralized fibers and/or mineralized bone fibers. These sheets are layered and stacked. Thus, in some embodiments, the osteoimplant is formed as a laminate. A laminate osteoimplant may advantageously be shaped in three dimensions, as in the introduction of a concave surface shape. Further, each layer of the laminate is continuous, without requiring binding of the joints between the pieces.

Assembling the superimposed layers into a strong unitary structure may be accomplished by a variety of means/ procedures, for example, application of known and conventional biologically compatible adhesives such as the cyano- acrylates; epoxy-based compounds, dental resin sealants, dental resin cements, glass ionomer cements, polymethyl methacrylate, gelatin-resorcinol-formaldehyde glues, collagen-based glues, inorganic bonding agents such as zinc phosphate, magnesium phosphate or other phosphate-based cements, zinc carboxylate, and protein-based binders such as fibrin glues and mussel-derived adhesive proteins; the use of mechanical fasteners such as pins, screws, dowels, which can be fabricated from natural or synthetic materials and bioabsorbable as well as nonbioabsorbable materials; laser tissue welding; and ultrasonic bonding. If desired, the layers of the osteogenic osteoimplant can be provided with mechanically interengaging features, for example, tongue-and-groove, mortise-and-tenon, or dove-tail elements, to facilitate their assembly into the final product and/or to fix the layers to each other in a more secure fashion. The optimal method of assembly would be determined on a case-by-case basis through routine experimentation. In addition to its carrier and osteoinductive layers, the osteoimplant of this embodiment can optionally possess one or more layers formed from one or more other materials or substances.

In another embodiment, the carrier may comprise a single thin sheet of material. The delivery systems thus may comprise a single thin sheet of material comprising carrier and demineralized fibers as disclosed herein. The sheet of material may be rolled or folded over itself.

For placement, the mixture of demineralized bone matrix and the mineralized bone fibers may be provided in a covering and the covering placed in vivo. In one embodiment, the covering is placed in vivo by placing the covering in a catheter or tubular inserter and delivering the covering with the catheter or tubular inserter. The covering, with a substance provided therein, may be steerable such that it can be used with flexible introducer instruments for, for example, minimally invasive spinal procedures. For example, the osteoimplant may be introduced down a tubular retractor or scope, during XLIF, TLIF, or other procedures. In other embodiments, the covering (with or without substance loaded) may be placed in a cage, for example for interbody fusion.

VII. Formulation

The carrier, the osteoinductive composition, the covering, or the osteoimplant may be formulated for a particular use. The formulation may be used to alter the physical, biological, or chemical properties of any component of the osteoimplant. A physician would readily be able to determine the formulation needed for a particular application, taking into account such factors as the type of injury, the site of injury, the patient's health, and the risk of infection. In various embodiments, the osteoinductive composition may comprise, for example less than approximately 0.5% water, less than approximately 1% water, or less than approximately 5% water.

Carriers, osteoinductive compositions, coverings, or osteoimplants therefore may be prepared to have selected resorption/loss of osteoinductivity rates, or even to have different rates in different portions of an implant. For example, the formulation process may include the selection of demineralized particles or fibers of a particular size or composition, combined with the selection of a particular stabilizing agent or agents, and the amounts of such agents.

Physical properties such as deformability and viscosity of the carrier may also be chosen depending on the particular clinical application. Further, the composition may be formulated to be settable and/or injectable. Thus, for example, the composition may be injectable through a needle, such as a 10-gauge, a 12-gauge, or an 18-gauge needle, as desired.

In the process of preparing the osteoimplant, the materials may be produced entirely aseptically or be sterilized to eliminate any infectious agents such as HIV, hepatitis B, or hepatitis C. The sterilization may be accomplished using antibiotics, irradiation, chemical sterilization (e.g., ethylene oxide), or thermal sterilization. Other methods known in the art of preparing DBM such as defatting, sonication, and lyophilization may also be used in preparing a DBM carrier. Since the biological activity of demineralized bone is known to be detrimentally affected by most terminal sterilization processes, care must be taken when sterilizing the inventive compositions.

VIII. Optional Additives

Optionally, other additives may be included in an osteoimplant or osteocomposition comprising bone fibers as disclosed herein. It will be appreciated that the amount of additive used will vary depending upon the type of additive, the specific activity of the particular additive preparation employed, and the intended use of the composition. The desired amount is readily determinable by the user. Any of a variety of medically and/or surgically useful optional substances can be incorporated in, or associated with, the osteoinductive factors either before, during, or after preparation of the osteogenic composition.

In certain embodiments, the additive is adsorbed to or otherwise associated with the osteoimplant or osteocomposition. The additive may be associated with the osteoimplant through specific or non-specific interactions, or covalent or noncovalent interactions. Examples of specific interactions include those between a ligand and a receptor, an epitope and/or an antibody. Examples of nonspecific interactions include hydrophobic interactions, electrostatic interactions, magnetic interactions, dipole interactions, van der Waals interactions, hydrogen bonding, etc. In certain embodiments, the additive is attached to the osteoimplant, for example, to the carrier, using a linker so that the additive is free to associate with its receptor or site of action in vivo. In other embodiments the additive is either covalently or non-covalently attached to the carrier. In certain embodiments, the additive may be attached to a chemical compound such as a peptide that is recognized by the carrier. In another embodiment, the additive is attached to an antibody, or fragment thereof, that recognizes an epitope found within the carrier. In certain embodiments at least additives are attached to the osteoimplant. In other embodiments at least three additives are attached to the osteoimplant. An additive may be provided within the osteoimplant in a sustained release format. Thus, delivery of an osteoactive agent in an osteoimplant may include micro- or nano-encapsulation. For example, the additive may be encapsulated within biodegradable nanospheres, or microspheres. In this method, an osteoactive agent (or bioactive agent) is first encapsulated in a suitable material, such as a bioresorbably polymer or hydrogel micro- or nano-particle. The encapsulated osteoactive agent then is immobilized onto or into the osteoimplant. The bioresorbably polymer/hydrogel may be designed to control release kinetics of the osteoactive agent.

Generally, bioactive agents including, for example, bone growth promoting factors may be added to compositions of bone formed as described herein. Further, factors that stop, remove, or reduce the activity of bone growth inhibitors may also be added.

It will be understood by those skilled in the art that the lists of optional substances herewith included are not intended to be exhaustive and that other materials may be admixed with bone-derived elements within the practice of the present invention.

Radiopaque substances may be added to impart radiopacity to the composition. Examples of substances imparting radiopacity include for example, fully mineralized bone particles, barium and iodine containing compounds or compositions, for example, barium sulfate and barium sulfate for suspension, iopanoic acid, and the like. Mineralized cancellous bone, mineralized cortical bone, and partially demineralized bone, in solid, particle or fiber form may be added to endow the material with radiopacity. When employed, substances imparting radiopacity will typically represent from about 1 to about 25 weight percent of the bone particle containing composition, calculated prior to forming the shaped material. U.S. Pat. No. 5,676,146 discusses radiopaque bone grafts and is herein incorporated by reference in its entirety.

Development of a vasculature around the implant site may also be important to forming new bone and/or cartilage tissues. Angiogenesis may be an important contributing factor for the replacement of new bone and cartilage tissues. In certain embodiments, angiogenesis is promoted so that blood vessels are formed at the site to allow efficient transport of oxygen and other nutrients and growth factors to the developing bone or cartilage tissue. Thus, angiogenesis promoting factors may be included in the osteoimplant to increase angiogenesis in that region. For example, class 3 semaphorins, e.g., SEMA3, controls vascular morphogenesis by inhibiting integrin function in the vascular system, Serini et al., Nature, (July 2003) 424:391-397, incorporated herein by reference, and may be included in the osteoimplant. Vascular Endothelial Growth Factor (VEGF) and other cystine-knot growth factors may be used as well.

The osteoconductive composition may provide a system for delivering bioactive agents, such as osteoinductive factors, to a host animal. Thus, the osteoimplant enables an improved healing response to the implant without the need to administer separately the bioactive agent. A problem with the introduction of the bioactive agent at the site is that it is often diluted and redistributed during the healing process by the circulatory systems (e.g., blood, lymph) of the recipient before complete healing has occurred. A solution to this problem of redistribution is to affix the bioactive components, including osteoactive agents, to the osteoimplant. Suitable bioactive agents and bioactive compounds are listed in the definition section of this application. Some preferred bioactive agents that can be delivered using a DBM composition include agents that promote the natural healing process, i.e., resorption, vascularization, angiogenesis, or new growth. In one embodiment, the osteoimplant is provided in which DBM, together with a stabilizing agent, is used to deliver the biologically active agent. It is expected that the stabilizing agent will protect the biologically active agent from degradation, and therefore will extend its active life after delivery into the recipient animal. In certain embodiments, the bioactive agent is an osteoinductive agent, and in certain embodiments, the DBM may be used to deliver more than one bioactive agent, preferably more than two, and more preferably sometimes more than three bioactive agents. The bioactive agent may be associated with the DBM. For example, the bioactive agent may be associated with the DBM through electrostatic interactions, hydrogen bonding, pi stacking, hydrophobic interactions, or van der Waals interactions. In certain embodiments, the bioactive agent is attached to the DBM through specific interactions such as those between a receptor and its ligand or between an antibody and its antigen. In other embodiments, the bioactive agent is attached to the DBM through non-specific interactions (e.g., hydrophobic interactions).

Medically/surgically useful substances include physiologically or pharmacologically active substances that act locally or systemically in the host. Generally, these substances may include bioactive substances which can be readily incorporated into the osteoimplant and include, e.g., demineralized bone powder as described in U.S. Pat. No. 5,073,373, the contents of which are incorporated herein by reference; collagen, insoluble collagen derivatives, and soluble solids and/or liquids dissolved therein; antiviricides, particularly those effective against HIV and hepatitis; antimicrobials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin and gentamycin; biocidal/biostatic sugars such as dextran, glucose; amino acids; peptides; vitamins; inorganic elements; co-factors for protein synthesis; hormones; endocrine tissue or tissue fragments; synthesizers; enzymes such as alkaline phosphatase, collagenase, peptidases, oxidases; polymer cell scaffolds with parenchymal cells; angiogenic agents and polymeric carriers containing such agents; collagen lattices; antigenic agents; cytoskeletal agents; cartilage fragments; living cells such as chondrocytes, bone marrow cells, mesenchymal stem cells; natural extracts; genetically engineered living cells or otherwise modified living cells; expanded or cultured cells; DNA delivered by plasmid, viral vectors or other means; tissue transplants; demineralized bone powder; autogenous tissues such as blood, serum, soft tissue, bone marrow; bioadhesives; bone morphogenic proteins (BMPs); osteoinductive factor (IFO); fibronectin (FN); endothelial cell growth factor (ECGF); vascular endothelial growth factor (VEGF); cementum attachment extracts (CAE); ketanserin; human growth hormone (HGH); animal growth hormones; epidermal growth factor (EGF); interleukins, for example, interleukin-1 (IL-1), interleukin-2 (IL-2); human alpha thrombin; transforming growth factor (TGF-beta); insulin-like growth factors (IGF-1, IGF-2); platelet derived growth factors (PDGF); fibroblast growth factors (FGF, BFGF, etc.); periodontal ligament chemotactic factor (PDLGF); enamel matrix proteins; growth and differentiation factors (GDF); hedgehog family of proteins; protein receptor molecules; small peptides derived from growth factors above; bone promoters; cytokines; somatotropin; bone digesters; antitumor agents; cellular attractants and attachment agents; immuno-suppressants; permeation enhancers, for example, fatty acid esters such as laureate, myristate and stearate monoesters of polyethylene glycol, enamine derivatives, alpha-keto aldehydes; and nucleic acids. The amounts of such optionally added substances can vary widely with optimum levels being readily determined in a specific case by routine experimentation.

In certain embodiments, the agent to be delivered is adsorbed to or otherwise associated with the osteoimplant. The agent may be associated with the osteoimplant through specific or non-specific interactions; or covalent or non-covalent interactions. Examples of specific interactions include those between a ligand and a receptor, a epitope and an antibody. Examples of non-specific interactions include hydrophobic interactions, electrostatic interactions, magnetic interactions, dipole interactions, van der Waals interactions, hydrogen bonding, etc. In certain embodiments, the agent is attached to the osteoimplant using a linker so that the agent is free to associate with its receptor or site of action in vivo. In certain embodiments, the agent to be delivered may be attached to a chemical compound such as a peptide that is recognized by the matrix of the DBM composition. In another embodiment, the agent to be delivered is attached to an antibody, or fragment thereof, that recognizes an epitope found within the matrix of the DBM composition. In a further embodiment, the agent is a BMP, TGF-.beta., IGF, parathyroid hormone (PTH), growth factors, or angiogenic factors. In certain embodiments at least two bioactive agents are attached to the DBM composition. In other embodiments at least three bioactive agents are attached to the DBM composition.

IX. Treatment of Compositions

In the process of preparing improved inventive bone and cartilage matrix materials, the materials may be produced entirely aseptically or be sterilized to eliminate any infectious agents including viruses, such as HIV, hepatitis B, or hepatitis C, as well as bacteria, mold, yeast, or other infectious agents. The sterilization may be accomplished using antibiotics, irradiation, chemical sterilization (e.g., ethylene oxide), or thermal sterilization. Other methods known in the art of preparing bone and cartilage matrices, such as defatting, sonication, and lyophilization may also be used in preparing the carrier. Since the biological activity of various materials including demineralized bone is known to be detrimentally affected by most terminal sterilization processes, care must be taken when sterilizing the inventive compositions. In some embodiments, the osteoimplants described herein will be prepared aseptically or sterilized.

These and other aspects of the present invention will be further appreciated upon consideration of the following Examples, which are intended to illustrate certain particular embodiments of the invention but are not intended to limit its scope, as defined by the claims.

EXAMPLES

Example 1

Combination of Demineralized and Mineralized Cartridge Milled Rabbit Fibers

A rabbit posterolateral fusion study was conducted with the subject MagniFuse® bone graft, the predicate MagniFuse® bone graft and autograft bone to compare the bone formation capabilities of the three materials. Autograft iliac crest bone was used as the control, since it is considered the "gold" standard for obtaining fusion in such surgeries. The rabbit posterolateral study design was chosen as it is a well-established model for evaluation of spinal fusion.

More specifically, the study was conducted to evaluate the ability to transition from pressed demineralized MagniFuse® fibers used in manufacturing the commercially available product to demineralized Grafton type fibers generated with a cartridge mill. Further, the surface demineralized chips contained in the commercially available product were replaced with mineralized Grafton type fibers generated with a cartridge mill. The mineralized fibers were used to provide mechanical support, osteoconductivity, and radio-opacity. A final ratio of 70% demineralized fibers and 30% mineralized fibers by volume ratio was utilized. This final ration translates to approximately 50 dry weight % of each type of fiber. This facilitates the manufacturing process, while maintaining visibility on x-ray and incorporating a high percentage of demineralized fibers.

The study considered three main groups of samples. Group 1 examined MagniFuse® in its current production form utilizing the MagniFuse "pressed" allograft fibers. This group represents the currently FDA cleared MagniFuse product (K082615) and served as a predicate group to group 2. Group 2 examined bone formation using a MagniFuse® DBM formulation containing a different processing than the commercial formula. It contained a combination of demineralized fibers (DBM) and mineralized fibers (50:50 based on weight, or 70:30 based on volume). This fiber/fiber allograft mix was delivered within a porous PGA mesh pouch as is done with commercial MagniFuse®). Group 3 represented the standard of care control group consisting of iliac crest bone autograft.

Graft Description

Group 1 MagniFuse® (predicate) was a predicate bone void filler cleared by FDA for use in extremities and in spine (K082615). It was a human bone allograft product containing human demineralized bone matrix (DBM) and surface demineralized cortical bone chips sealed in an absorbable mesh pouch to aide in intraoperative handling. It was both osteoinductive and osteoconductive. These properties were confirmed via on-going osteoinductivity testing in a validated assay. For this study, MagniFuse® was prepared following methods equivalent to those used to make human MagniFuse®, with the exception that rabbit bone was used in place of human bone. This change was made to prevent immune rejection of xenogeneic tissue in this immune-competent model. In this study, 3 cc cylindrical (1 cm diameter) grafts were manufactured according to standard methods and stored in a barrier system designed to maintain graft stability. These grafts were hydrated with saline at the time of surgery just prior to placement into the prepared grafting site in the rabbit posterolateral spine. 3 cc grafts were placed bilaterally at the operated level at the time of implantation such that the graft fully spanned the prepared transverse processes according to the IBEX surgical technique.

Group 2 MagniFuse® demineralized fiber/mineralized fiber implants were prepared following methods analogous to those that will be used to make human MagniFuse® demineralized fiber/mineralized fiber implants, with the exception that rabbit bone was used in place of human bone. This change was made to prevent immune rejection of xenogeneic tissue in this immune-competent model.

Rabbit bone was milled using a top loading cartridge mill. Mineralized rabbit bone segments and demineralized rabbit bone segments were placed in a mold, covered with water, frozen at −70°, and milled separately for each fiber type. Mineralized fibers were subjected to super critical $CO_2$ treatment analogous to the chips contained in the commercial Magnifuse product to ensure appropriate viral inactivation. Demineralized rabbit bone fibers were maintained wet, mineralized rabbit bone fibers were maintained dry and rehydrated for packaging into the mesh pouch. Mineralized and demineralized bone fibers were combined by calculating 30% mineralized fiber to 70% demineralized fiber by volume and manually manipulated to ensure uniform mixture. Each graft consisted of 3 cc total fibers inserted into a mesh pouch which was then subsequently sealed. Grafts were subjected to critical point drying, and lyophilization and then packaged two per foil pouch to maintain their dehydrated condition. All graft preparations were completed under aseptic conditions. Grafts were hydrated with saline at the time of surgery just prior to placement into the prepared grafting site in the rabbit posterolateral spine. 3 cc grafts were placed bilaterally at the operated level at the time of implantation such that the graft fully spanned the prepared transverse processes according to the IBEX surgical technique.

Group 3 autograft was studied in this example as a control group to ensure model consistency with the literature and to ensure validity of the test model employed. Autograft was obtained bilaterally from the iliac crest of all animals enrolled in group 7. Approximately 6.0 cc of autograft bone was obtained from each animal such that bilateral 3 cc beds of morselized autogenous bone could be laid into the posterolateral spine at the operated level to fully span the prepared transverse processes according to the IBEX surgical technique. This group represented the standard of care control group.

Surgical Procedure

Following anesthetization and skin preparation, a dorsal midline incision was made over the lumbar region of the operated animal. Blunt and sharp dissection was employed to expose the dorsal surface of the transverse processes of the two adjacent L4/L5 vertebra of the lumbar spine. A motorized bur was used to remove the dorsal cortex of bone revealing the central marrow space such that bleeding bone was achieved. Great care was taken to avoid disruption of the facet joints at the operated segment. Based on group assignment, graft material was applied to fully span the prepared transverse processes. In the case of autograft animals randomized to group 7, a prior procedure to recover autograft from the iliac crest was performed. Autograft recovery was unilateral or bilateral based on the group assignment of the animal and the amount of autograft required. After graft placement, musculature was repositioned and the wound closed in layers. Animals were then recovered from anesthesia and individually housed for the duration of the study.

This study evaluated the bone forming characteristics of each of three test groups by implanting bone grafts in decorticated paraspinal beds bridging the L4 and L5 transverse processes in 6 New Zealand rabbits for each of the three test groups. Each animal received two implants of the same graft (one on each side of the spine). To avoid immune rejection, rabbit bone was used to prepare the subject and predicate MagniFuse® Bone grafts, instead of human bone. All other manufacturing procedures were kept the same. Table 1 below outlines the implant distribution in the study. After 8 weeks each animal was evaluated using a combination of manual palpation and radiography. Radiographs using a faxitron were taken prior to surgery, immediately post-surgery and at 8 weeks, just prior to necropsy.

TABLE 1

R&D Study Study Group

| Group | Number of Animals | Graft Type | Total # of Implants |
|---|---|---|---|
| 1 | 6 | Predicate MagniFuse ® Bone graft | 12 |
| 2 | 6 | Subject MagniFuse ® Bone Graft | 12 |
| 3 | 6 | Autograft Iliac Crest | 12 |

The manual palpation results show no difference between the three study groups, indicating that the subject MagniFuse® is equivalent to the predicate and to autograft with respect to bone formation. The radiographic results also indicated comparable results between the three study groups (83% for autograft, 92% for the subject MagniFuse® and 92% for the predicate MagniFuse®). Table 2 below provides palpation and radiographic results.

TABLE 2

8-Week Manual Palpation and Radiographic Results

| Group | Treatment Group | Manual Palpation % Fused | Radiographic Results % Fused |
|---|---|---|---|
| 1 | MagniFuse ® Bone graft (Predicate) | 83 (10/12) | 92 (11/12) |
| 2 | Modified MagniFuse ® Bone graft (Subject) | 83 (10/12) | 92 (11/12) |
| 3 | Iliac Crest Autograft | 83 (10/12) | 83 (10/12) |

In this in vivo study both subject and predicate MagniFuse® bone graft implants showed remodeling and fusion rates comparable to each other and to autograft bone.

Example 2

Osteoinductivity Testing

Subject and predicate MagniFuse® bone graft samples were also evaluated for osteoinductivity in an athymic rat ectopic bone model. Samples of the subject MagniFuse® and predicate MagniFuse® bone grafts were implanted in intermuscular hind limb locations in athymic rats and evaluated histologically for bone formation after 28 days.

For each specimen, 40 mg material was weighed for implantation. The samples were rehydrated with 100 µl of sterile saline, heat sealed in a biodegradable mesh bag, and placed into an appropriately labeled, blunt-cut, 1 cc syringe for delivery of the implant. Syringes were sorted, packaged into self-seal pouches by animal number according to randomized surgical procedure, such that the same animal did not have the same donor in both hind limbs. The packaged samples were stored in the lab refrigerator until the time of surgery and were implanted within 3 days.

Osteoinductivity testing followed OTI standard procedures ASM-005, TMD-005, TMD-006, TMD-008, and TMD-010 where applicable. The study was conducted on the female athymic Hsd:RH-foxn1$^{nu}$ rat, obtained at 4-5 weeks of age from Harlan (Indianapolis, Ind.). The rats were acclimated for at least one week prior to surgery in sterile microisolator cages, with sterile water and rodent diet provided. Aseptic surgical procedure were carried out in a laminar flow hood. For surgical implantation, a single intermuscular site in each hind limb of the rat was used. After a period of 28 days, the animals were euthanized with $CO_2$ and implants were retrieved by blunt dissection for histological processing.

The OI results showed bone formation in both groups, with OI scores of 3.13±0.8 for the predicate MagniFuse® and 3.25±0.5 for the subject MagniFuse®.

The results of these studies indicate that the subject MagniFuse® is substantially equivalent to the predicate MagniFuse® with respect to fusion and osteoinductivity. Based on these findings, the subject MagniFuse® Bone graft is substantially equivalent to the predicate MagniFuse® Bone graft.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. An osteoinductive composition implantable into a mammal, the composition comprising a mixture of demineralized bone fibers and fully mineralized bone fibers disposed in a biodegradable polymer mesh covering comprising polyglycolic acid (PGA), wherein the mixture comprises demineralized bone fibers in an amount from about 30 vol % to about 45 vol % and fully mineralized bone fibers in an amount from about 55 vol % to about 70 vol %, and the demineralized bone fibers have an average length from about 2.1 cm to about 9 cm, and the biodegradable polymer mesh covering is a bag having at least one compartment, and the at least one compartment comprises a first compartment comprising the demineralized bone fibers and a second compartment comprising the fully mineralized bone fibers.

2. An osteoinductive composition according to claim 1, wherein the mixture is visible under X ray and remodels.

3. An osteoinductive composition according to claim 1, wherein the mixture further comprises autograft bone.

4. An osteoinductive composition according to claim 1, wherein after implantation at a surgical site for about 28 days the mixture exhibited an osteoinductivity of about 3.2.

5. An osteoinductive composition according to claim 1, wherein the demineralized bone fibers are comprised in a demineralized bone matrix.

6. An osteoinductive composition according to claim 1, wherein the aspect ratio of the elongated demineralized bone fiber is from about 50:1 to about 1000:1, from about 50:1 to about 950:1, from about 50:1 to about 750:1, from about 50:1 to about 500:1, from about 50:1 to about 250:1, from about 50:1 to about 100:1, from about 10:1 to about 50:1, or from about 5:1 to about 10:1.

7. An osteoinductive composition according to claim 1, further comprising an additive selected from collagen, collagen derivatives, antiviricides, antimicrobials, antibiotics, biocidal sugars, amino acids, peptides, vitamins, inorganic elements, co-factors for protein synthesis, hormones, endocrine tissue, endocrine tissue fragments, enzymes, polymer cell scaffolds with parenchymal cells, angiogenic drugs, collagen lattices, antigenic agents, cytoskeletal agents, cartilage fragments, living cells, natural extracts, tissue transplants, demineralized bone powder, autogenous tissues, bioadhesives, bone morphogenetic proteins (BMPs), angiogenic factors, transforming growth factor (TGF-beta), insulin-like growth factor (IGF-1), growth hormones, bone digestors, antitumor agents, immuno-suppressants, permeation enhancers, enamine derivatives, nucleic acids or combinations thereof.

8. An osteoinductive composition according to claim 1, further comprising at least one additive selected from stem cells, autograft bone marrow aspirate, autograft bone, preparations of selected autograft cells, autograft cells containing genes encoding bone promoting action, autograft cells expanded outside the body and returned or combinations thereof.

9. An osteoinductive composition according to claim 1, further comprising adhesives, fillers, plasticizers, flexibilizing agents, biostatic/biocidal agents, surface active agents, binding and bonding agents.

10. An osteoinductive composition according to claim 1, further comprising a carrier, the carrier comprising collagen; synthetic hydroxyapatites; polymers; hydrogels; starches; polyethylene glycol, tricalcium phosphate, sintered hydroxyapatite, settable hydroxyapatite; polylactic acid; tyrosine polycarbonate; calcium sulfate; collagen sheets; settable calcium phosphate; polymeric cements; settable poly vinyl alcohols, polyurethanes; resorbable polymers; polysaccharides and other large polymers; or liquid settable polymers.

11. A delivery system comprising a biodegradable polymer mesh covering comprising polyglycolic acid (PGA) having at least one compartment, the covering comprising an osteoinductive implantable composition comprising a mixture of demineralized fibers and fully mineralized fibers in a ratio from about 1:1.2 to about 1:2.3, and the mixture comprises demineralized bone fibers in an amount from about 30 vol % to about 45 vol % and fully mineralized bone fibers in an amount from about 55 vol % to about 70 vol %, and the demineralized bone fibers have an average length from about 2.1 cm to about 9 cm, and the biodegradable polymer mesh covering is a bag, and the at least one compartment comprises a first compartment comprising the demineralized bone fibers and a second compartment comprising the fully mineralized bone fibers.

12. A delivery system according to claim 11, wherein the demineralized bone fibers are contained in a demineralized bone matrix.

13. A method of treating a bone defect caused by injury, disease, wounds, or surgery comprising administering surgically at the bone defect site to a patient in need thereof an effective amount of an osteoinductive implantable composition according to claim 1 disposed in a biodegradable polymer mesh covering comprising polyglycolic acid (PGA), and the composition comprises a mixture of demineralized bone fibers in an amount from about 30 vol % to about 45 vol % and fully mineralized bone fibers in an amount from about 55 vol % to about 70 vol %, and the demineralized bone fibers have an average length from about 2.1 cm to about 9 cm, and the biodegradable polymer mesh covering is a bag having at least one compartment, and the at least one compartment comprises a first compartment comprising the demineralized bone fibers and a second compartment comprising the fully mineralized bone fibers, wherein the covering has a modulus of elasticity in the range of about $1 \times 10^2$ to about $6 \times 10^5$.

14. An osteoinductive composition according to claim 7, wherein the additive is encapsulated within biodegradable nanospheres to provide a sustained release of the additive.

15. An osteoinductive composition according to claim 1, wherein the osteoinductive composition further comprises a plasticizer comprising glycerol, monacetin, or diacetin.

16. An osteoinductive composition according to claim 1, wherein the covering has a modulus of elasticity in the range of about $1 \times 10^2$ to about $6 \times 10^5$.

17. An osteoinductive composition according to claim 1, wherein the composition consists of a mixture of demineralized bone fibers and fully mineralized bone fibers disposed in a biodegradable polymer mesh covering consisting of polyglycolic acid (PGA), wherein the mixture consists of demineralized bone fibers in an amount from about 30 vol % to about 45 vol % and fully mineralized bone fibers in an amount from about 55 vol % to about 70 vol %, and the demineralized bone fibers have an average length from about 2.1 cm to about 9 cm, and the biodegradable polymer mesh covering is a bag having at least one compartment, and the at least one compartment consists of a first compartment consisting of the demineralized bone fibers and a second compartment consisting of the fully mineralized bone fibers and the covering has a modulus of elasticity in the range of about $1 \times 10^2$ to about $6 \times 10^5$.

* * * * *